United States Patent
Ortyn et al.

(10) Patent No.: US 8,131,053 B2
(45) Date of Patent: Mar. 6, 2012

(54) DETECTION OF CIRCULATING TUMOR CELLS USING IMAGING FLOW CYTOMETRY

(75) Inventors: William Ortyn, Bainbridge Island, WA (US); David Basiji, Seattle, WA (US); Luchuan Liang, Woodinville, WA (US); Vidya Venkatachalam, Bellevue, WA (US); Philip Morrissey, Bellevue, WA (US)

(73) Assignee: Amnis Corporation, Seattle, WA (US)

( * ) Notice: Subject to any disclaimer, the term of this patent is extended or adjusted under 35 U.S.C. 154(b) by 834 days.

(21) Appl. No.: 12/181,062

(22) Filed: Jul. 28, 2008

(65) Prior Publication Data
US 2008/0317325 A1 Dec. 25, 2008

Related U.S. Application Data

(63) Continuation-in-part of application No. 11/344,941, filed on Feb. 1, 2006, now Pat. No. 7,522,758, and a continuation of application No. 11/123,610, filed on May 4, 2005, now Pat. No. 7,450,229, and a continuation-in-part of application No. 10/628,662, filed on Jul. 28, 2003, now Pat. No. 6,975,400, which is a continuation-in-part of application No. 09/976,257, filed on Oct. 12, 2001, now Pat. No. 6,608,682, which is a continuation-in-part of application No. 09/820,434, filed on Mar. 29, 2001, now Pat. No. 6,473,176, which is a continuation-in-part of application No. 09/538,604, filed on Mar. 29, 2000, now Pat. No. 6,211,955, which is a continuation-in-part of application No. 09/490,478, filed on Jan. 24, 2000, now Pat. No. 6,249,341.

(60) Provisional application No. 60/952,522, filed on Jul. 27, 2007, provisional application No. 60/649,373, filed on Feb. 1, 2005, provisional application No. 60/567,911, filed on May 4, 2004, provisional application No. 60/117,203, filed on Jan. 25, 1999, provisional application No. 60/240,125, filed on Oct. 12, 2000.

(51) Int. Cl.
*G06K 9/00* (2006.01)
*G01J 3/28* (2006.01)

(52) U.S. Cl. .................. 382/133; 356/326
(58) Field of Classification Search .............. 382/128, 382/133, 134; 600/410, 562; 356/451, 456, 356/326
See application file for complete search history.

(56) References Cited

U.S. PATENT DOCUMENTS
3,497,690 A  2/1970 Gunter et al. .............. 250/461.2
(Continued)

FOREIGN PATENT DOCUMENTS
EP  0 154 404  9/1985
(Continued)

OTHER PUBLICATIONS

Amann et al., "Fluorescent-Oligonucleotide Probing of Whole Cells for Determinative, Phylogenetic, and Environmental Studies in Microbiology," *Journal of Bacteriology* vol. 172, No. 2: 762-770, Feb. 1990.

(Continued)

*Primary Examiner* — Rochelle-Ann J Blackman
(74) *Attorney, Agent, or Firm* — Law Office of Ronald M. Anderson

(57) ABSTRACT

Photometric and morphometric features derived from multi-mode imagery of cells in flow are used as a cell analyzer to determine if a marker corresponding to a cancer cell or pre-cancerous cell is present in the population of cells imaged. An imaging system simultaneously acquires a plurality of images for each cell passing through the field of view of the imaging system. Acquiring a plurality of different images (i.e., bright field, dark field, and fluorescent images) facilitates the determination of different morphological and morphometric parameters. Simultaneously acquiring the plurality of images enables relatively large populations of cells to be rapidly imaged, so that relatively small numbers of cancer cells in a large population of cells can be detected. Initially, known cancer cells are imaged to enable a marker to be identified. Then, a sample that may include cancer cells is imaged to determine if the marker is present.

21 Claims, 17 Drawing Sheets

U.S. PATENT DOCUMENTS

| | | | |
|---|---|---|---|
| 3,555,280 A | 1/1971 | Richards, Jr. | 250/201 |
| 3,586,760 A | 6/1971 | Dillenburger | 348/339 |
| 3,922,069 A | 11/1975 | Kishikawa et al. | 359/633 |
| 4,313,734 A | 2/1982 | Leuvering | 23/230 |
| 4,414,575 A | 11/1983 | Yamamoto et al. | 348/350 |
| 4,635,293 A | 1/1987 | Watanabe | 382/130 |
| 4,662,742 A | 5/1987 | Chupp | 356/39 |
| 4,677,680 A | 6/1987 | Harima et al. | 382/112 |
| 4,703,017 A | 10/1987 | Campbell et al. | 436/501 |
| 4,737,932 A | 4/1988 | Baba | 364/900 |
| 4,770,992 A | 9/1988 | Van den Engh et al. | 435/6 |
| 4,777,525 A | 10/1988 | Preston, Jr. | 348/111 |
| 4,786,165 A | 11/1988 | Yamamoto et al. | 356/23 |
| 4,845,197 A | 7/1989 | Petersen et al. | 530/387 |
| 4,857,453 A | 8/1989 | Ullman et al. | 435/7 |
| 5,096,807 A | 3/1992 | Leaback | 435/6 |
| 5,107,522 A | 4/1992 | Kitayama et al. | 375/97 |
| 5,122,453 A | 6/1992 | Martin et al. | 435/7.24 |
| 5,141,609 A | 8/1992 | Sweedler et al. | 356/344 |
| 5,153,916 A | 10/1992 | Inagaki et al. | 382/151 |
| 5,159,397 A | 10/1992 | Kosaka et al. | 356/73 |
| 5,159,398 A | 10/1992 | Maekawa et al. | 356/73 |
| 5,159,642 A | 10/1992 | Kosaka | 382/6 |
| 5,247,339 A | 9/1993 | Ogino | 356/73 |
| 5,247,340 A | 9/1993 | Ogino | 356/73 |
| 5,257,182 A | 10/1993 | Luck et al. | 364/413.1 |
| 5,272,354 A | 12/1993 | Kosaka | 250/574 |
| 5,351,311 A | 9/1994 | Rogers | 382/156 |
| 5,372,936 A | 12/1994 | Fraatz et al. | 435/34 |
| 5,422,712 A | 6/1995 | Ogino | 356/73 |
| 5,436,144 A | 7/1995 | Stewart et al. | 435/91.2 |
| 5,444,527 A | 8/1995 | Kosaka | 356/73 |
| 5,459,240 A | 10/1995 | Foxwell et al. | 530/328 |
| 5,471,294 A | 11/1995 | Ogino | 356/73 |
| 5,547,849 A | 8/1996 | Baer et al. | 435/7.24 |
| 5,548,349 A | 8/1996 | Mizuguchi et al. | 348/766 |
| 5,548,395 A | 8/1996 | Kosaka | 356/73 |
| 5,568,315 A | 10/1996 | Shuman | 359/487 |
| 5,596,401 A | 1/1997 | Kusuzawa | 356/23 |
| 5,621,460 A | 4/1997 | Hatlestad et al. | 348/265 |
| 5,625,048 A | 4/1997 | Tsien et al. | 536/23.4 |
| 5,633,503 A | 5/1997 | Kosaka | 250/458.1 |
| 5,644,388 A | 7/1997 | Maekawa et al. | 356/73 |
| 5,674,743 A | 10/1997 | Ulmer | 435/287.2 |
| 5,686,960 A | 11/1997 | Sussman et al. | 348/335 |
| 5,695,934 A | 12/1997 | Brenner | 435/6 |
| 5,733,721 A | 3/1998 | Hemstreet, III et al. | 435/6 |
| 5,754,291 A | 5/1998 | Kain | 356/344 |
| 5,760,899 A | 6/1998 | Eismann | 356/326 |
| 5,764,792 A | 6/1998 | Kennealy | 382/133 |
| 5,784,162 A * | 7/1998 | Cabib et al. | 356/456 |
| RE35,868 E | 8/1998 | Kosaka | 250/574 |
| 5,828,776 A | 10/1998 | Lee et al. | 382/133 |
| 5,831,723 A | 11/1998 | Kubota et al. | 356/73 |
| 5,844,670 A | 12/1998 | Morita et al. | 356/124 |
| 5,848,123 A | 12/1998 | Strommer | 378/98.8 |
| 5,855,753 A | 1/1999 | Trau et al. | 204/484 |
| 5,900,942 A | 5/1999 | Spiering | 356/400 |
| 5,926,283 A | 7/1999 | Hopkins | 356/419 |
| 5,929,986 A | 7/1999 | Slater et al. | 356/326 |
| 5,959,953 A | 9/1999 | Alon | 369/44.41 |
| 5,985,549 A | 11/1999 | Singer et al. | 435/6 |
| 5,986,061 A | 11/1999 | Petska | 530/352 |
| 6,007,994 A | 12/1999 | Ward et al. | 435/6 |
| 6,007,996 A | 12/1999 | McNamara et al. | 435/6 |
| 6,014,468 A | 1/2000 | McCarthy et al. | 382/254 |
| 6,066,459 A | 5/2000 | Garini et al. | 435/6 |
| 6,108,082 A | 8/2000 | Pettipiece et al. | 356/326 |
| 6,115,119 A | 9/2000 | Sieracki et al. | 356/337 |
| 6,116,739 A | 9/2000 | Ishihara et al. | 353/31 |
| 6,156,465 A | 12/2000 | Cao et al. | 430/30 |
| 6,159,686 A | 12/2000 | Kardos et al. | 435/6 |
| 6,210,973 B1 | 4/2001 | Pettit | 436/172 |
| 6,211,955 B1 | 4/2001 | Basiji et al. | 356/326 |
| 6,229,913 B1 | 5/2001 | Nayar et al. | 382/154 |
| 6,249,314 B1 | 6/2001 | Yamamoto et al. | 348/242 |
| 6,249,341 B1 | 6/2001 | Basiji et al. | 356/73 |
| 6,256,096 B1 | 7/2001 | Johnson | 356/335 |
| 6,259,807 B1 | 7/2001 | Ravkin | 382/133 |
| 6,330,081 B1 | 12/2001 | Scholten | 358/463 |
| 6,330,361 B1 | 12/2001 | Mitchell et al. | 382/211 |
| 6,381,363 B1 | 4/2002 | Murching et al. | 382/164 |
| 6,473,176 B2 | 10/2002 | Basiji et al. | 356/326 |
| 6,507,391 B2 | 1/2003 | Basiji et al. | 356/28 |
| 6,519,355 B2 | 2/2003 | Nelson | 382/133 |
| 6,522,781 B1 | 2/2003 | Norikane et al. | 382/203 |
| 6,532,061 B2 | 3/2003 | Basiji et al. | 356/28 |
| 6,548,259 B2 | 4/2003 | Ward et al. | 435/6 |
| 6,549,664 B1 | 4/2003 | Daiber et al. | 382/232 |
| 6,563,583 B2 | 5/2003 | Ortyn et al. | 356/400 |
| 6,580,504 B1 | 6/2003 | Basiji et al. | 356/338 |
| 6,583,865 B2 | 6/2003 | Basiji et al. | 356/73 |
| 6,608,680 B2 | 8/2003 | Basiji et al. | 356/338 |
| 6,608,682 B2 | 8/2003 | Ortyn et al. | 356/419 |
| 6,618,140 B2 | 9/2003 | Frost et al. | 356/317 |
| 6,620,591 B1 | 9/2003 | Dunlay et al. | 435/7.2 |
| 6,658,143 B2 | 12/2003 | Hansen et al. | 382/133 |
| 6,671,044 B2 | 12/2003 | Ortyn et al. | 356/326 |
| 6,671,624 B1 | 12/2003 | Dunlay et al. | 702/19 |
| 6,707,551 B2 | 3/2004 | Ortyn et al. | 356/338 |
| 6,716,588 B2 | 4/2004 | Sammak et al. | 435/7.23 |
| 6,727,066 B2 | 4/2004 | Kaser | 435/6 |
| 6,763,149 B2 | 7/2004 | Riley et al. | 382/294 |
| 6,778,263 B2 | 8/2004 | Ortyn et al. | 356/28 |
| 6,873,733 B2 | 3/2005 | Dowski, Jr. | 382/232 |
| 6,875,973 B2 | 4/2005 | Ortyn et al. | 250/201.3 |
| 6,906,792 B2 | 6/2005 | Ortyn et al. | 356/28.5 |
| 6,927,922 B2 | 8/2005 | George et al. | 359/708 |
| 6,934,408 B2 | 8/2005 | Frost et al. | 382/129 |
| 6,947,128 B2 | 9/2005 | Basiji et al. | 356/73 |
| 6,947,136 B2 | 9/2005 | Ortyn et al. | 356/338 |
| 6,975,400 B2 | 12/2005 | Ortyn et al. | 356/419 |
| 7,006,710 B2 | 2/2006 | Riley et al. | 382/294 |
| 7,033,819 B2 | 4/2006 | Kim et al. | 435/29 |
| 7,042,639 B1 | 5/2006 | McDowell | 359/398 |
| 7,050,620 B2 | 5/2006 | Heckman | 382/133 |
| 7,057,732 B2 | 6/2006 | Jorgenson et al. | 356/445 |
| 7,079,708 B2 | 7/2006 | Riley et al. | 382/294 |
| 7,087,877 B2 | 8/2006 | Ortyn et al. | 250/201.2 |
| 7,139,415 B2 | 11/2006 | Finkbeiner | 382/128 |
| 7,180,673 B2 | 2/2007 | Dowski, Jr. | 359/637 |
| 7,190,832 B2 | 3/2007 | Frost et al. | 382/173 |
| 7,221,457 B2 | 5/2007 | Jorgenson et al. | 356/445 |
| 7,289,205 B2 | 10/2007 | Yaroslavsky et al. | 356/417 |
| 7,315,357 B2 | 1/2008 | Ortyn et al. | 356/73 |
| 7,450,229 B2 | 11/2008 | Ortyn et al. | 356/326 |
| 7,567,695 B2 | 7/2009 | Frost et al. | 382/129 |
| 7,667,761 B2 | 2/2010 | Thomas | 348/335 |
| 2001/0006416 A1 | 7/2001 | Johnson | 356/73 |
| 2001/0011018 A1 | 8/2001 | Baum et al. | 455/439 |
| 2001/0012620 A1 | 8/2001 | Rich | 435/7.1 |
| 2002/0030812 A1 | 3/2002 | Ortyn et al. | 356/326 |
| 2002/0126275 A1 | 9/2002 | Johnson | 356/317 |
| 2002/0146734 A1 | 10/2002 | Ortyn et al. | 435/6 |
| 2003/0048931 A1 | 3/2003 | Johnson et al. | 382/128 |
| 2003/0049701 A1 | 3/2003 | Muraca | 435/7.23 |
| 2003/0059093 A1 | 3/2003 | Rosania et al. | 382/128 |
| 2003/0104439 A1 | 6/2003 | Finch | 435/6 |
| 2004/0093166 A1 | 5/2004 | Kil | 702/19 |
| 2004/0111220 A1 | 6/2004 | Ochs et al. | 702/19 |
| 2004/0241759 A1 | 12/2004 | Tozer et al. | 435/7.2 |
| 2005/0014129 A1 | 1/2005 | Cliffel et al. | 435/4 |
| 2006/0246481 A1 | 11/2006 | Finch et al. | 435/6 |
| 2006/0257884 A1 | 11/2006 | Brawley et al. | 435/6 |
| 2007/0054350 A1 | 3/2007 | Walker, Jr. | 435/34 |
| 2008/0240539 A1 | 10/2008 | George et al. | 382/133 |
| 2009/0202130 A1 | 8/2009 | George et al. | 382/133 |

FOREIGN PATENT DOCUMENTS

| | | |
|---|---|---|
| EP | 0 280 559 | 8/1988 |
| EP | 0 281 327 | 6/1993 |
| EP | 0 372 707 | 3/1996 |
| EP | 0 950 890 | 10/1999 |
| EP | 1 316 793 | 6/2003 |
| WO | WO 88/08534 | 11/1988 |
| WO | WO 90/10715 | 9/1990 |
| WO | WO 95/20148 | 7/1995 |

| | | |
|---|---|---|
| WO | WO 97/26333 | 7/1997 |
| WO | WO 98/53093 | 11/1998 |
| WO | WO 98/53300 | 11/1998 |
| WO | WO 99/24458 | 5/1999 |
| WO | WO 99/64592 | 12/1999 |
| WO | WO 00/06989 | 2/2000 |
| WO | WO 00/14545 | 3/2000 |
| WO | WO 00/42412 | 7/2000 |
| WO | WO 01/11341 | 2/2001 |
| WO | WO 01/46675 | 6/2001 |
| WO | WO 02/17622 A | 2/2002 |
| WO | WO 02/18537 | 3/2002 |
| WO | WO 02/31182 | 4/2002 |
| WO | WO 02/35474 | 5/2002 |
| WO | WO 02/073200 | 9/2002 |
| WO | WO 02/079391 | 10/2002 |
| WO | WO 2005/90945 | 9/2005 |
| WO | WO 2005/98430 | 10/2005 |

OTHER PUBLICATIONS

Arkesteijn et al., "Chromosome Specific DNA Hybridization in Suspension for Flow Cytometric Detection of Chimerism in Bone Marrow Transplantation and Leukemia," *Cytometry* 19: 353-360, Apr. 1995.

Bains et al., "Flow Cytometric Quantitation of Sequence-Specific mRNA in Hemopoietic Cell Suspension by Primer-Induced in Situ (PRINS) Fluorescent Nucleotide Labeling," *Experimental Cell Research* 208: 321-326, Sep. 1993.

Barren III et al., "Method for Identifying Prostate Cells in Semen Using Flow Cytometry," *The Prostate* 36: 181-188, 1998.

Bauman et al., "Flow Cytometric Detection of Ribosomal RNA in Suspended Cells by Fluorescent In Situ Hybridization," *Cytometry* 9: 517-524, 1988.

Baumgartner et al., "Automated Evaluation of Frequencies of Aneuploid Sperm by Laser-Scanning Cytometry (LSC)," *Cytometry* 44: 156-160, 2001.

Ben-Eliezer et al., "All-optical extended depth of field imaging system," *Journal of Optics A: Pure and Applied Optics* 5: S164-S169, 2003.

Biggs et al., "Acceleration of iterative image restoration algorithms" *Applied Optics* vol. 36, No. 8: 1766-1775, Mar. 10, 1997.

Boyle et al., "Isolation and Initial Characterization of a Large Repeat Sequence Element Specific to Mouse Chromosome 8," *Genomics* vol. 12, No. 3: 517-525, 1992.

Callet-Bauchu et al., "Distribution of the cytogenetic abnormality +i(3)(q10) in persistent polyclonal B-cell lymphocytosis: a FICTION study in three cases," *British Journal of Haematology* 99: 531-536, Dec. 1997.

Ding et al., "Characterization and Quantitation of NF-κB Nuclear Translocation Induced by Interleukin-1 and Tumor Necrosis Factor-α," *The Journal of Biological Chemistry* vol. 273, No. 44: 28897-28905, Oct. 30, 1998.

Disteche et al., "Isolation and characterization of two repetitive DNA fragments located near the centromere of the mouse X chromosome," *Cytogenetics and Cell Genetics* 39: 262-268, 1985.

Dragowska et al., "Measurement of DNA repeat sequence by flow cytometry," *Cytometry* Supplement 7: 51, Oct. 1994.

Engvall, Eva. "Enzyme Immunoassay ELISA and EMIT," *Methods in Enzymology* vol. 70, Part A: 419-439, 1980.

Fernandez-Lago et al., "Fluorescent Whole-Cell Hybridization with 16S rRNA-Targeted Oligonucleotide Probes to Identify *Brucella* spp. by Flow Cytometry," *Journal of Clinical Microbiology* vol. 38, No. 7: 2768-2771, Jul. 2000.

George et al., "Extended depth of field using a logarithmic asphere" *Journal of Optics A: Pure and Applied Optics* 5: S157-S163, 2003.

Hultdin et al., "Telomere analysis by fluorescence in situ hybridization and flow cytometry," *Nucleic Acids Research* vol. 26, No. 16: 3651-3656, Aug. 15, 1998.

Lauzon et al., "Flow Cytometric Measurement of Telomere Length," *Cytometry* 42: 159-164, Jun. 2000.

Levron et al., "Sperm chromosome abnormalities in men with severe male factor infertility who are undergoing in vitro fertilization with intracytoplasmic sperm injection," *Fertility and Sterility* vol. 76, No. 3: 479-484, Sep. 2001.

Lowe et al., "Aneuploid epididymal sperm detected in chromosomally normal and Robertsonian translocation-bearing mice using a new three-chromosome FISH method," *Chromosoma* 105: 204-210, 1996.

Majno et al., "Apoptosis, Oncosis, and Necrosis *An Overview of Cell Death*," *American Journal of Pathology* vol. 146, No. 1: 3-15, Jan. 1, 1995.

Martin et al., "Detection of aneuploidy in human interphase spermatozoa by fluorescence in situ hybridization (FISH)," *Cytogenetics and Cell Genetics* 64: 23-26, 1993.

Nautiyal et al., "17β-Estradiol induces nuclear translocation of CrkL at the window of embryo implantation," *Biochemical and Biophysical Research Communications* 318: 103-112, 2004.

Ortyn et al., "Extended Depth of Field Imaging for High Speed Cell Analysis" *Cytometry Part A* 71A: 215-231, 2007.

Pala et al., "Flow cytometric measurement of intracellular cytokines," *Journal of Immunological Methods* 243: 107-124, 2000.

Pang et al., "Detection of aneuploidy for chromosomes 4, 6, 7, 8, 9, 10, 11, 12, 13, 17, 18, 21, X and Y by fluorescence in-situ hybridization in spermatozoa from nine patients with oligoasthenoteratozoospermia undergoing intracytoplasmic sperm injection," *Human Reproduction* vol. 14, No. 5: 1266-1273, 1999.

Patterson et al., "Detection of HIV-1 DNA and Messenger RNA in Individual Cells by PCR-Driven in Situ Hybridization and Flow Cytometry," *Science* 260: 976-979, May 14, 1993.

Perreault et al., "The Role of Disulfide Bond Reduction during Mammalian Sperm Nuclear Decondensation in Vivo," *Developmental Biology* 101: 160-167, 1984.

Pinkel et al., "Cytogenetic analysis using quantitative, high sensitivity, fluorescence hybridization," *Proceedings of the National Academy of Sciences: Genetics* 83: 2934-2938, 1986.

Pollice et al., "Sequential Paraformaldehyde and Methanol Fixation for Simultaneous Flow Cytometric Analysis of DNA, Cell Surface Proteins, and Intracellular Proteins," *Cytometry* 13: 432-444, 1992.

Ried et al., "Simultaneous visualization of seven different DNA probes by in situ hybridization using combinatorial fluorescence and digital imaging microscopy," *Proceedings of the National Academy of Sciences: Genetics* 89: 1388-1392, Feb. 1992.

Robbins et al., "Aneuploidy in sperm of Hodgkin's disease patients receiving NOVP chemotherapy," *The American Journal of Human Genetics* vol. 55, No. 3 —Supplement: A68 (371), Sep. 1994.

Robbins et al., "Detection of Aneuploid Human Sperm by Fluorescence In Situ Hybridization: Evidence for a Donor Difference in Frequency of Sperm Disomic for Chromosomes I and Y," *The American Journal of Human Genetics*, 52: 799-807, 1993.

Robbins et al., "Three-probe Fluorescence in situ Hybridization to Assess Chromosome X, Y, and 8 Aneuploidy in Sperm of 14 Men from Two Healthy Groups: Evidence for a Paternal Age Effect on Sperm Aneuploidy," *Reproduction, Fertility and Development* 7: 799-809, 1995.

Robbins et al., "Use of Fluorescence In Situ Hybridization (FISH) to Assess Effects of Smoking, Caffeine, and Alcohol on Aneuploidy Load in Sperm of Healthy Men," *Environmental and Molecular Mutagenesis* 30: 175-183, 1997.

Rufer et al., "Telomere length dynamics in human lymphocyte subpopulations measured by flow cytometry," *Nature Biotechnology* 16: 743-747, Aug. 1998.

Salzman et al., "Light Scatter: Detection and Usage," *Current Protocols in Cytometry* Supplement 9: 1.13.1-1.138.8, 1999.

Schmid et al., "Evaluation of inter-scorer and inter-laboratory reliability of the mouse epididymal sperm aneuploidy (m-ESA) assay," *Mutagenesis* vol. 16, No. 3: 189-195, 2001.

Schmid et al., "Simultaneous Flow Cytometric Analysis of Two Cell Surface Markers, Telomere Length, and DNA Content," *Cytometry* 49: 96-105, 2002.

Schwerin et al., "Quantification of Y Chromosome Bearing Spermatozoa of Cattle Using In Situ Hybridization," *Molecular Reproduction and Development* 30: 39-43, 1991.

Shi et al., "Aneuploidy in human sperm: a review of the frequency and distribution of aneuploidy, effects of donor age and lifestyle factors," *Cytogenetics and Cell Genetics* 90: 219-226, 2000.

Timm et al., "Amplification and Detection of a Y-Chromosome DNA Sequence by Fluorescence In Situ Polymerase Chain Reaction and Flow Cytometry Using Cells in Suspension," *Cytometry (Communications in Clinical Cytometry)* 22: 250-255, 1995.

Timm et al., "Fluorescent In Situ Hybridization En Suspension (FISHES) Using Digoxigenin-qLabeled Probes and Flow Cytometry," *Biotechniques* vol. 12, No. 3: 362-367, 1992.

Trask et al., "Fluorescence in situ hybridization to interphase cell nuclei in suspension allows flow cytometric analysis of chromosome content and microscopic analysis of nuclear organization," *Human Genetics* 78:251-259, 1988.

Tucker et al., "Extended depth of field and aberration control for inexpensive digital microscope systems" *Optics Express* vol. 4, No. 11: 467-474, May 24, 1999.

van Dekken et al., "Flow Cytometric Quantification of Human Chromosome Specific Repetitive DNA Sequences by Single and Bicolor Fluorescent In Situ Hybridization to Lymphocyte Interphase Nuclei," *Cytometry* 11: 153-164, 1990.

van den Berg et al., "Detection of Y Chromosome by In situ Hybridization in Combination with Membrane Antigens by Two-Color Immunofluorescence," *Laboratory Investigation* vol. 64, No. 5: 623-628, 1991.

Weber-Matthieson et al., "Rapid immunophenotypic characterization of chromosomally aberrant cells by the new FICTION method," *Cytogenetics Cell Genetics* 63: 123-125, 1993.

Weber-Matthieson et al., "Simultaneous Fluorescence Immunophenotyping and Interphase Cytogenetics: A Contribution to the Characterization of Tumor Cells," *Journal of Histochemistry and Cytochemistry* vol. 40, No. 2: 171-175, 1992.

Wyrobek et al., "Smokers produce more aneuploid sperm than non-smokers," *The American Society of Human Genetics*, 45th Annual Meeting, A131: 737, Oct. 24-28, 1995.

Wyrobek et al., "Detection of Sex Chromosomal Aneuploidies X-X, Y-Y, and X-Y, in Human Sperm Using Two-Chromosome Fluorescence In Situ Hybridization," *American Journal of Medical Genetics* 53: 1-7, 1994.

Wyrobek et al., "Fluorescence In Situ Hybridization to Y Chromosomes in Decondensed Human Sperm Nuclei," *Molecular Reproduction and Development* 27: 200-208, 1990.

Oberholzer et al., "Methods in quantitative image analysis." *Histochem Cell Biol*, vol. 105: 333-355, 1996.

George, Thaddeus, David A. Basiji, Brian E. Hall, David H. Lynch, William E. Ortyn, David J. Perry, Michael J. Seo, Cathleen A. Zimmerman, and Philip J. Morrissey. "Distinguishing Modes of Cell Death Using the ImageStream® Multispectral Imaging Flow Cytometer" *Cytometry Part A* 59A:237-245 (2004).

George, Thaddeus C., Stacey L. Fanning, Patricia Fitzgeral-Bocarsly, Ricardo B. Medeiros, Sarah Highfill, Yoji Shimizu, Brian E. Hall, Keith Frost, David Basiji, William E. Ortyn, Philip J. Morrissey, David H. Lynch. "Quantitative measurement of nuclear translocation events using similarity analysis of multispectral cellular images obtained in flow," Journal of Immunological Methods 311 (2006) 117-129.

Gordy, Claire et al., "Visualization of antigen presentation by actin-mediated targeting of glycolipid-enriched membrane domains to the immune synapse of B cell APCs." Journal of Immunology, vol. 172, No. 4, Feb. 15, 2004. pp. 2030-2038, XP002481372 ISSN: 0022-1767.

Hecht, Eugene. "Optics 4th ed." 2002. Addison-Wesley Longman, Inc., XP-002465391. ISBN: 0-8053-8566-5.

Kubota, Fumio et al. 1995. "Flow Cytometer and Imaging Device Used in Combination." *Cytometry*: 21:129-132.

Kubota, F. 2003. "Analysis of red cell and platelet morphology using an imaging-combined flow cytometer." *Clin. Lab. Haem.*: 25:71-76.

Ong, Sim Heng. 1985. Development of a System for Imaging and Classifying Biological Cells in a Flow Cytometer. Doctor of Philosophy Thesis. University of Sydney, School of Electrical Engineering. (August).

Ong, S.H. et al. 1987. "Development of an Image Flow Cytometer." *Analytical and Quantitative Cytology and Histology. XIVth International Conference on Medical and Biological Engineering and the VIIth International Conference on Medical Physics*, Finland. (August): 375-382.

Ong, S.H. and P.M. Nickolls. 1991. "Optical Design in a Flow System for Imaging Cells." *Sciences in Medicine*: 14:2:74-80.

Ong, S.H. and P.M. Nickolls. 1994. "Analysis of MTF Degradation in the Imaging of Cells in a Flow System." *International Journal of Imaging Systems & Technology*: 5:243-250.

Satoh, Kaneo et al. 2002. "Small Aggregates of Platelets Can Be Detected Sensitively by a Flow Cytometer Equipped With an Imaging Device: Mechanisms of Epinephrine-Induced Aggregation and Antiplatelet Effects of Beraprost." *Cytometry*: 48:194-201.

Wang, Fu-sheng and Fumio Kubota. 2002. "A Novel Apoptosis Research Method With Imaging-Combined Flow Cytometer and HITC OR IR-125 Staining " *Cytometry*: 50:267-274.

Wietzorrek, Joachim et al. 1999. "A New Multiparameter Flow Cytometer: Optical and Electrical Cell Analysis in Combination With Video Microscopy in Flow." *Cytometry*: 35:291-301.

Ferraro et al., "Extended focused image in microscopy by digital holography." *Optics Express*, vol. 13, No. 18: 6738-6749, 2005.

* cited by examiner

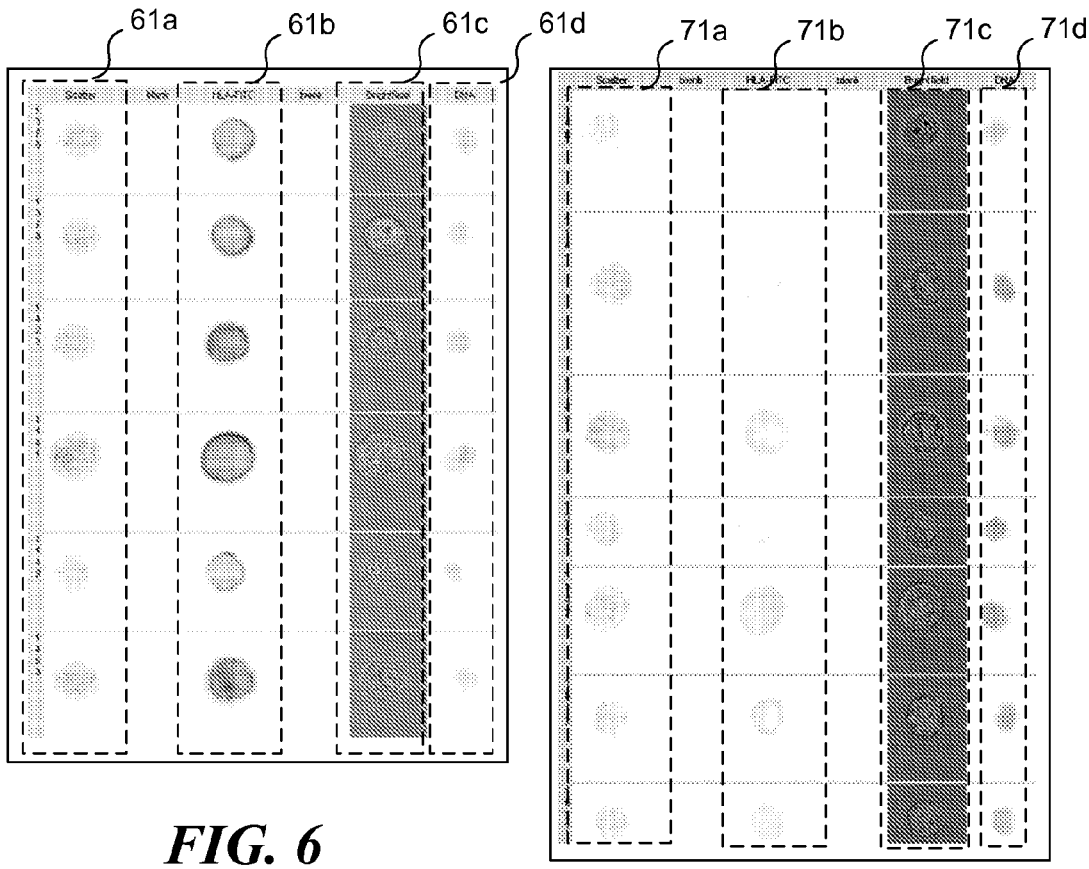
*FIG. 6*
*FIG. 7*
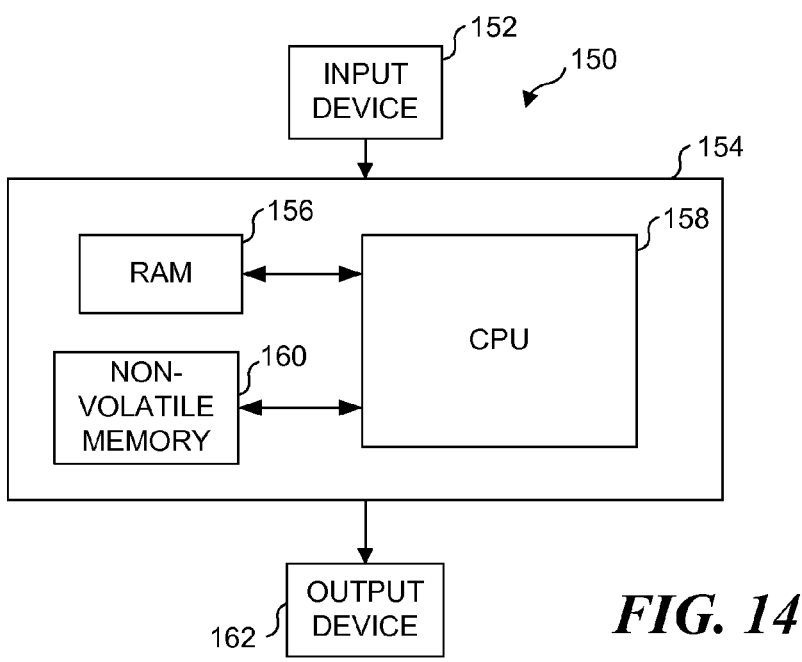
*FIG. 14*

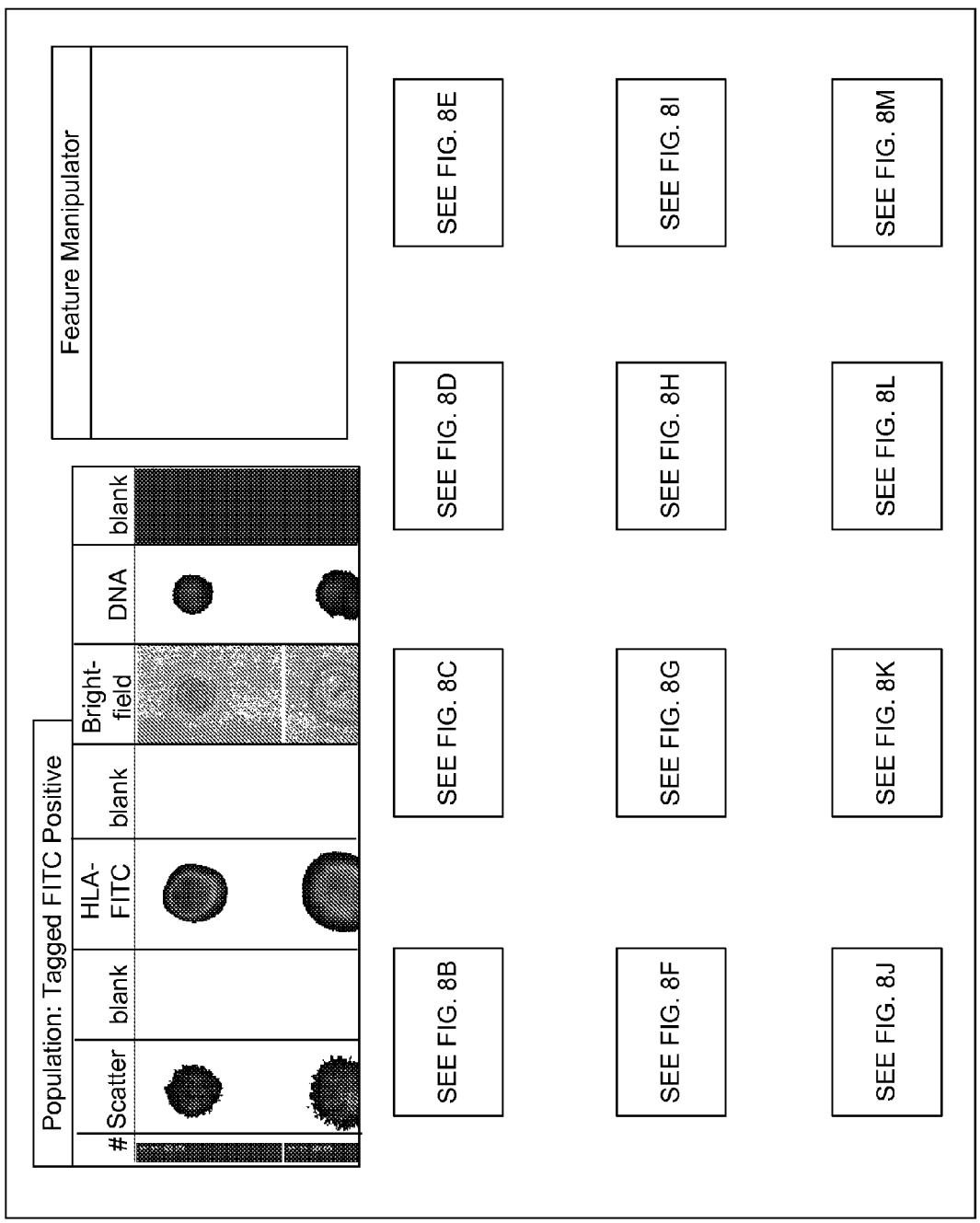

# DETECTION OF CIRCULATING TUMOR CELLS USING IMAGING FLOW CYTOMETRY

RELATED APPLICATIONS

This application is based on a prior copending provisional application, Ser. No. 60/952,522, filed on Jul. 27, 2007, the benefit of the filing date of which is hereby claimed under 35 U.S.C. §119(e). This application is a continuation-in-part of a copending patent application, Ser. No. 11/344,941, filed on Feb. 1, 2006, which itself is based on a prior provisional application, Ser. No. 60/649,373, filed on Feb. 1, 2005, the benefits of the filing dates of which are hereby claimed under 35 U.S.C. §119(e) and 35 U.S.C. §120.

Patent application Ser. No. 11/344,941 is also a continuation application based on a prior conventional application, Ser. No. 11/123,610, filed on May 4, 2005, which itself is based on a prior provisional application, Ser. No. 60/567,911, filed on May 4, 2004, and which is also a continuation-in-part of prior patent application Ser. No. 10/628,662, filed on Jul. 28, 2003, which issued as U.S. Pat. No. 6,975,400 on Dec. 13, 2005, which itself is a continuation-in-part application of prior patent application Ser. No. 09/976,257, filed on Oct. 12, 2001, which issued as U.S. Pat. No. 6,608,682 on Aug. 19, 2003, which itself is a continuation-in-part application of prior patent application Ser. No. 09/820,434, filed on Mar. 29, 2001, which issued as U.S. Pat. No. 6,473,176 on Oct. 29, 2002, which itself is a continuation-in-part application of prior patent application Ser. No. 09/538,604, filed on Mar. 29, 2000, which issued as U.S. Pat. No. 6,211,955 on Apr. 3, 2001, which itself is a continuation-in-part application of prior application patent application Ser. No. 09/490,478, filed on Jan. 24, 2000, which issued as U.S. Pat. No. 6,249,341 on Jun. 19, 2001, which itself is based on prior provisional patent application Ser. No. 60/117,203, filed on Jan. 25, 1999, the benefit of the filing dates of which is hereby claimed under 35 U.S.C. §120 and 35 U.S.C. §119(e). patent application Ser. No. 09/976,257, noted above, is also based on prior provisional application Ser. No. 60/240,125, filed on Oct. 12, 2000, the benefit of the filing date of which is hereby claimed under 35 U.S.C. §119(e).

BACKGROUND

Carcinomas are the most common form of cancer, and are responsible for the majority of cancer-related deaths worldwide. Early detection of cancer improves a prognosis significantly, as evidenced by the 70% reduction in mortality in cervical cancer after the Papanicolaou test became accepted as a routine annual examination in the United States. Likewise, mortality rates from breast cancer have been reduced by up to 30% because of earlier detection through manual examination and mammograms. Unfortunately, the relative inaccessibility of most body tissues currently limits the breadth of cancer screening. Even when tumors are detected by existing techniques and removed surgically, there is a strong inverse correlation between tumor size and out-come, such that cancer survival rates are higher when tumors are detected early and removed while the tumors are relatively small in size.

The analysis of accessible body fluids for the detection of neoplastic cells should greatly facilitate earlier cancer detection, and the detection of micro-metastases in body fluids of patients who have early stage cancer could have a substantial impact on optimizing therapeutic regimens and, thus, long-term prognosis. Unfortunately, even when cancer is present in a patient, the relative number of cancer cells in readily accessible bodily fluids such as blood is generally quite small, making cancer detection by sampling bodily fluids very challenging. Classic microscopy-based analysis, although the gold standard in diagnostics, lacks the throughput required to identify rare cell populations consistently and with confidence. Flow cytometry offers much higher data acquisition rates, but flow cytometery depends largely on the availability of fluorescently labeled markers to discriminate between normal cells and neoplastic cells, and tumor-specific markers generally have not yet been identified.

The use of an antibody-based approach to address this problem depends on ectopic expression of a normal antigenic epitope, formation of a new epitope through genetic mutation or recombination, or consistent modulation of the expression of a marker expressed in transformed and non-transformed cells. The approach is confounded further by the diversity of neoplastic transformations and genetic heterogeneity in the human population.

In contrast to single- or multi-parameter antibody-based techniques, cellular morphology analysis is an effective means of cancer screening. For instance, dysplastic and neoplastic cells are detected in lung sputum on the basis of morphology. Likewise, exfoliated cells collected from bladder washings of bladder cancer patients are shown to have distinct morphologic and genetic changes. Dysplastic morphology is also the primary diagnostic criterion in Papanicolaou smears, where microscope-based auto-mated morphologic analysis is shown to be effective and approved by the Food and Drug Administration for primary screening.

Studies have indicated that cancer cells exhibit morphological characteristics that can be used to differentiate cancer cells from normal cells, however, most instruments capable of acquiring cellular images having enough detail to enable such morphological characteristics to be discerned do not have the throughput required to be able to detect very small numbers of cancer cells hidden in relatively large populations of normal cells. This problem is significant, because studies have indicated that the blood of a majority of patients who have had metastatic carcinomas contains fewer than one detectable carcinoma cell per 7.5 mL of blood, which is below the current threshold of five circulating tumor cells necessary to make a statistically robust diagnosis.

It would be desirable to provide a method and apparatus configured to rapidly acquire detailed cellular images from relatively large populations of cells, such that relatively small numbers of cancer cells present in a larger population can be statistically detected.

SUMMARY

This application specifically incorporates herein by reference, the disclosures and drawings of each patent application and issued patent identified above as a related application.

The present disclosure provides methods of using both photometric and morphometric features derived from multi-mode imagery of cells in flow. Such imaging methods can be employed for analyzing cells to determine if a marker corresponding to a cancer cell or precancerous cell is present in the population of cells imaged.

Preferably the population of cells is imaged while entrained in a fluid flowing through an imaging system. Imaging in flow enables image data to rapidly be acquired from a relatively large population of cells. Furthermore, imaging cells in flow facilitates sample preparation, since cells in bodily fluids can be imaged with very minimal sample preparation.

The imaging system employed to acquire the image data for the population of cells can be configured to simultaneously acquire a plurality of images for each cell passing through the field of view of the imaging system. Acquiring a plurality of different images is desirable, because utilizing different types of images (i.e., bright field images, dark field images, and fluorescent images) facilitates the determination of different morphological and morphometric parameters. Indeed, some such parameters cannot be obtained using only a single image. Simultaneously acquiring the plurality of different images is desirable because acquiring each different image at successive times would substantially increase image acquisition time, meaning that acquiring image data for a relatively large population of cells would take much longer than would be desirable.

Image data for a population of cells can be analyzed to detect cancer as follows. First, one or more markers or characteristics that can be measured from images collected by the imaging system used to image the population of cells is correlated to cancer cells (or precancerous cells). Once such a marker has been identified, a sample of bodily fluid from a patient can be very rapidly and easily analyzed to determine if that sample includes any cells having the identified marker.

An exemplary detection method includes the steps of using an imaging system to collect image data from a first population of biological cells where cancer or a precancerous condition is known to be present, and also, to collect image data from a second population of biological cells, where the cell population includes only normal, healthy cells. If either the healthy cells or the cancerous/precancerous cells are fluorescently labeled (and can therefore be distinguished using the image data), the first and second cell populations can be combined and imaged together. At least one photometric or morphometric marker associated with the cancerous condition is identified. Such a marker relates to identifying a photometric and/or morphometric difference between healthy cells and cancerous/precancerous cells. As described in greater detail below, exemplary markers include, but are not limited to, differences in the average nucleus size between healthy cells and carcinoma cells, and differences in the images of healthy cells and carcinoma cells. These differences can be quantified by processing the image data for the population of cells.

Once a photometric and/or morphometric marker associated with the cancerous condition is identified, image data are collected from a sample of a bodily fluid acquired from a patient (where it is not known if the patient has cancer). Image data are collected for the sample, and then the image data are analyzed to detect the presence of the previously identified marker, to determine whether cancer or a precancerous condition is present in the sample from the patient.

Significantly, where the imaging systems described below are used to collect the image data from a population of cells, the image data can be collected quite rapidly. In general, the analysis (i.e., analyzing the collected image data to either initially identify a marker or to determine the presence of a previously identified marker in a population of cells) can be performed off-line, i.e., after the collection of the image data. Current implementations of imaging processing software are capable of analyzing a relatively large population of cells (e.g., tens of thousands of cells) within tens of minutes using readily available personal computers. However, it should be recognized that as more powerful computing systems are developed and become readily available, it may become possible to analyze the image data in real-time. Thus, off-line processing of the image data is intended to be exemplary, rather than limiting, and it is contemplated that real-time processing of the image data is an alternative.

It should be noted that different types of cancer will likely exhibit different markers. Thus, the initial steps of analyzing images of known cancer cells and normal cells will likely be repeated to identify markers for different types of cancer cells. Populations of abnormal cells that are not cancerous, but which may be indicative of a precancerous condition (i.e., neoplastic cells), can also be imaged to identify similar markers.

Aspects of the concepts disclosed herein relate to a system and method for imaging and analyzing biological cells entrained in a flow of fluid. In at least one exemplary embodiment, a plurality of images of biological cells are collected simultaneously. The plurality of images include at least two of the following types of images: a bright field image, a dark field image, and a fluorescent image. Images are collected for a population of biological cells. Once the images have been collected, the images can be processed to identify a subpopulation of images, where the subpopulation shares photometric and/or morphometric characteristics empirically determined to be associated with a cancerous condition.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figure 3:
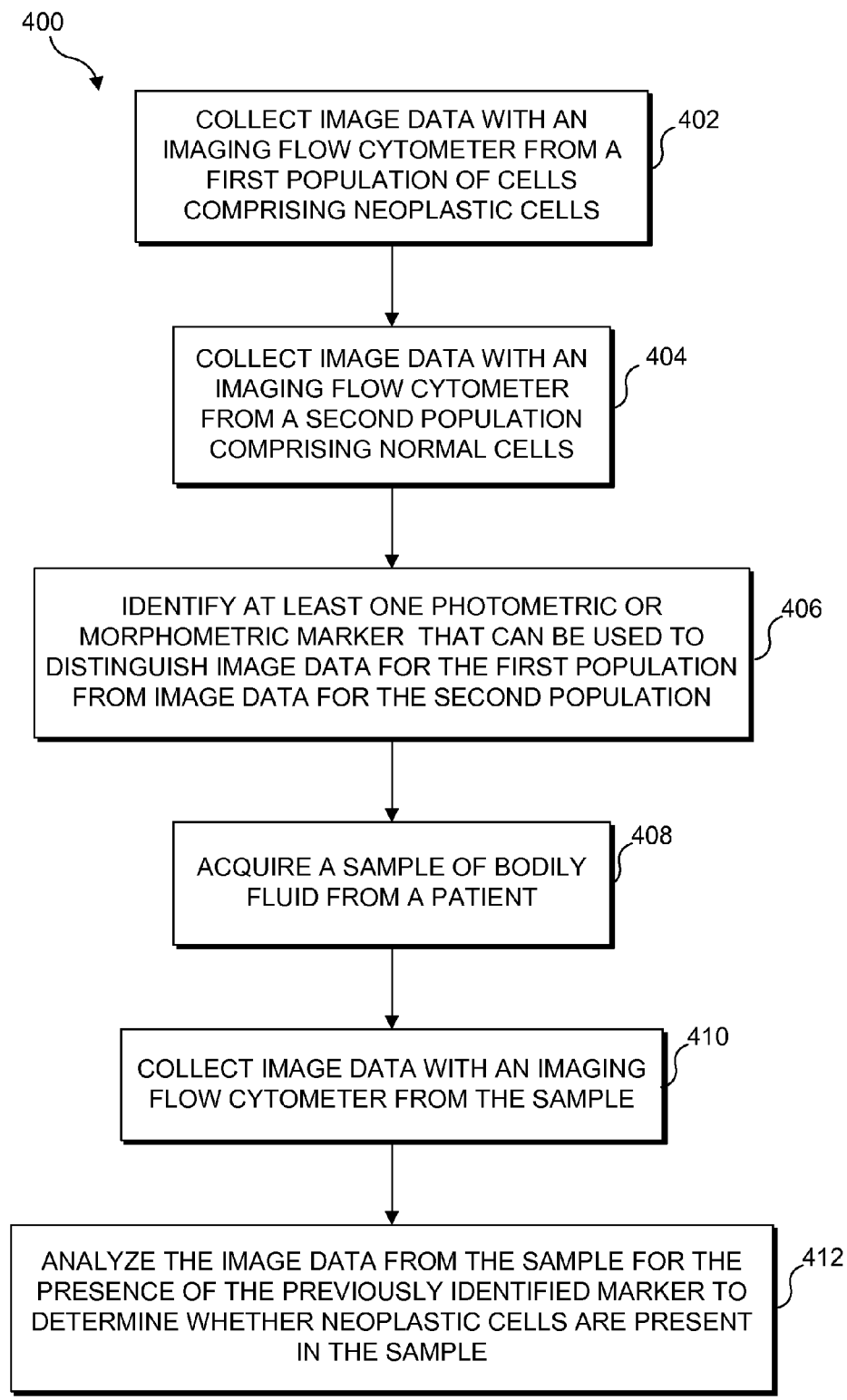
FIG. 3 is a flow chart of the overall method steps implemented in one aspect of the concepts disclosed herein.
Figure 9:
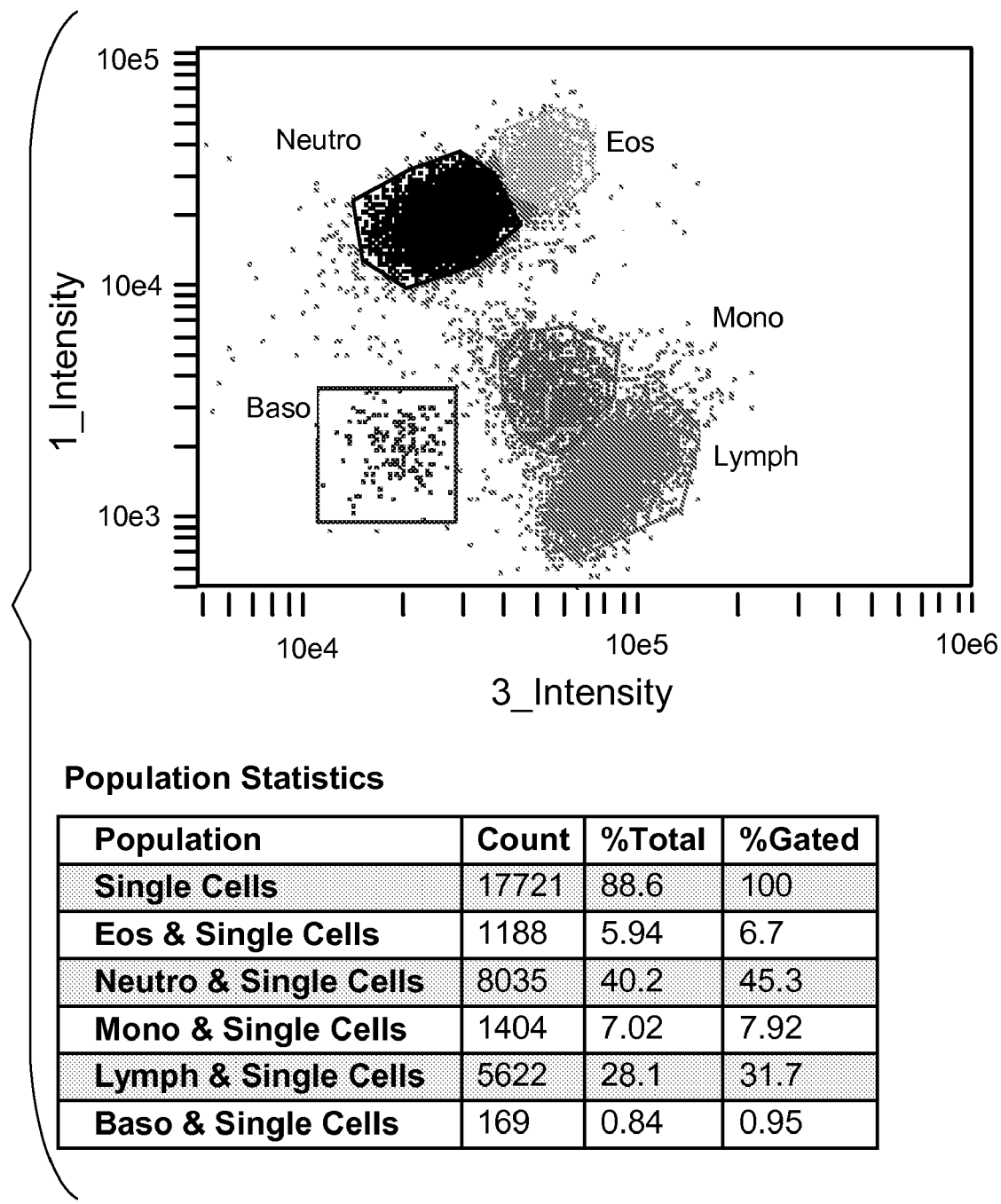
Figure 10A:
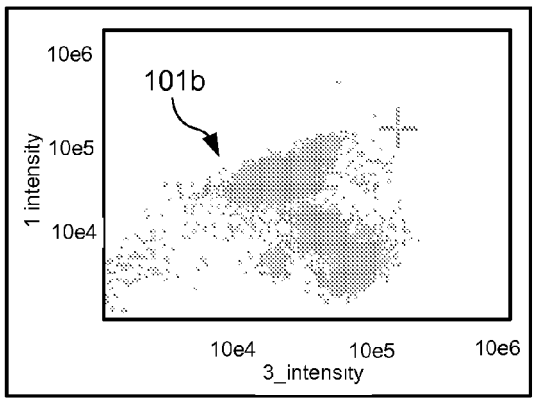
Figure 10B:
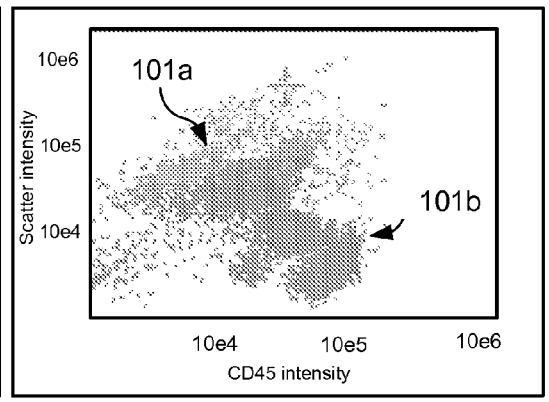
Figure 11A:
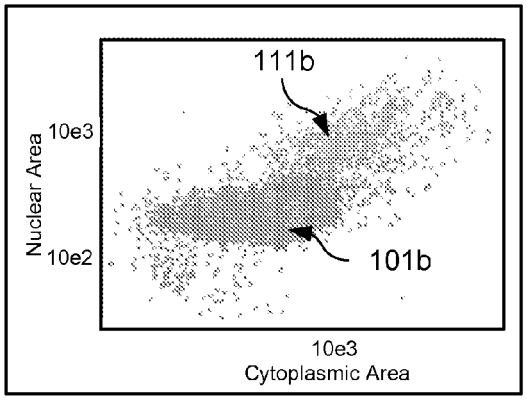
Figure 11B:
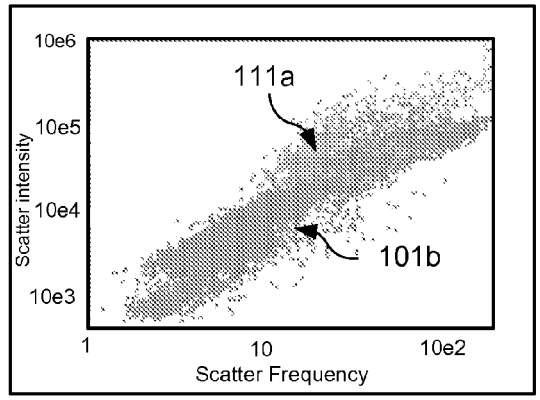
Figure 13:
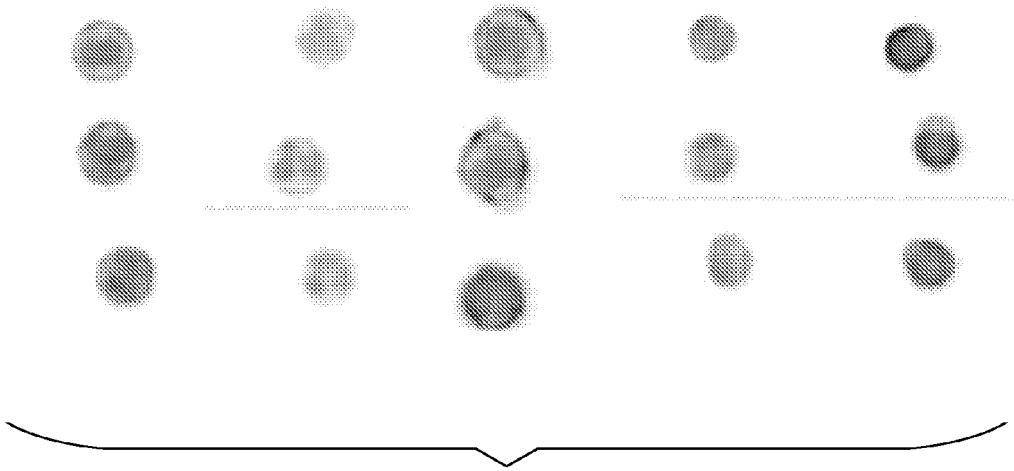
Figure 12:
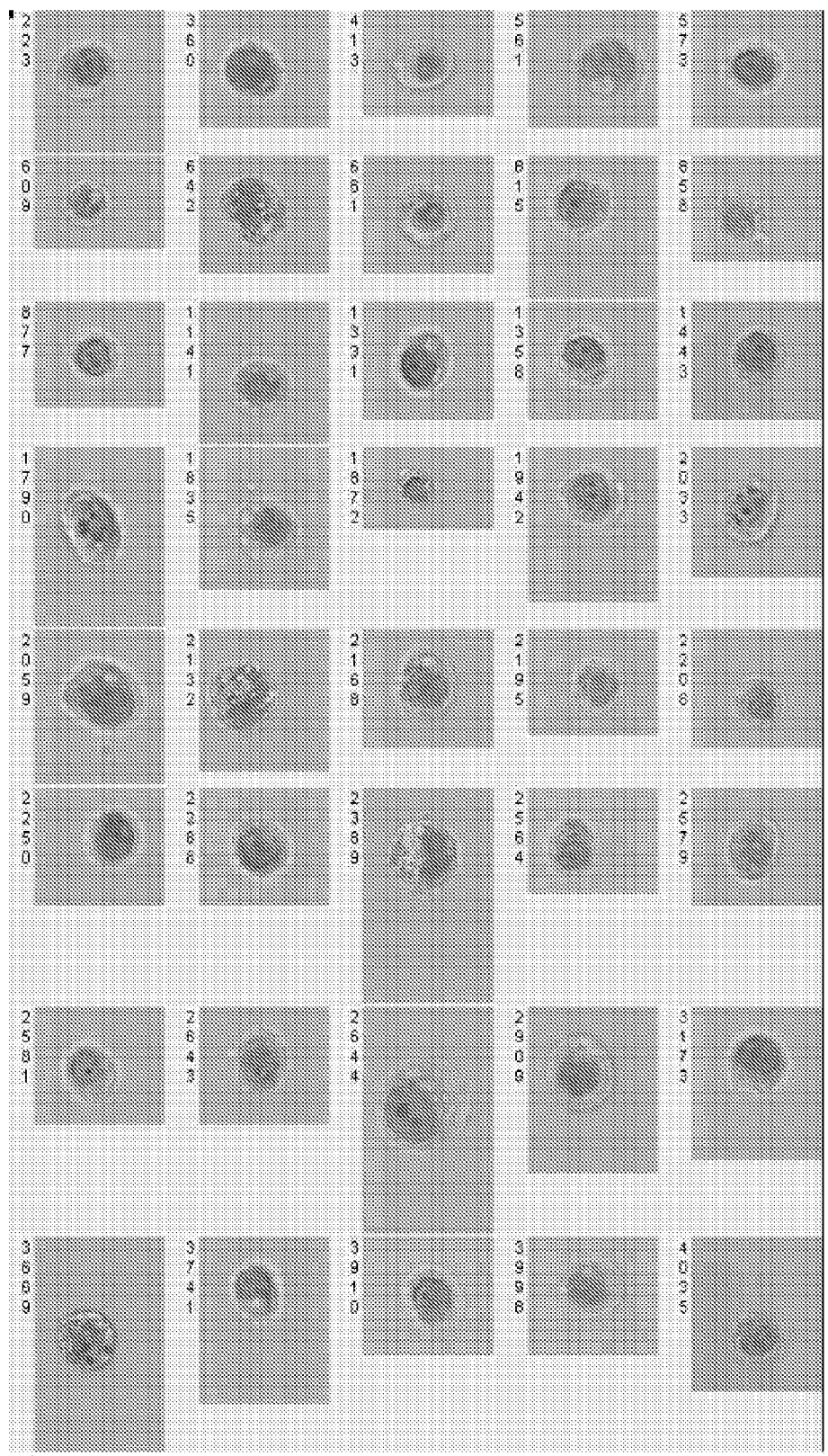
Figure 15:
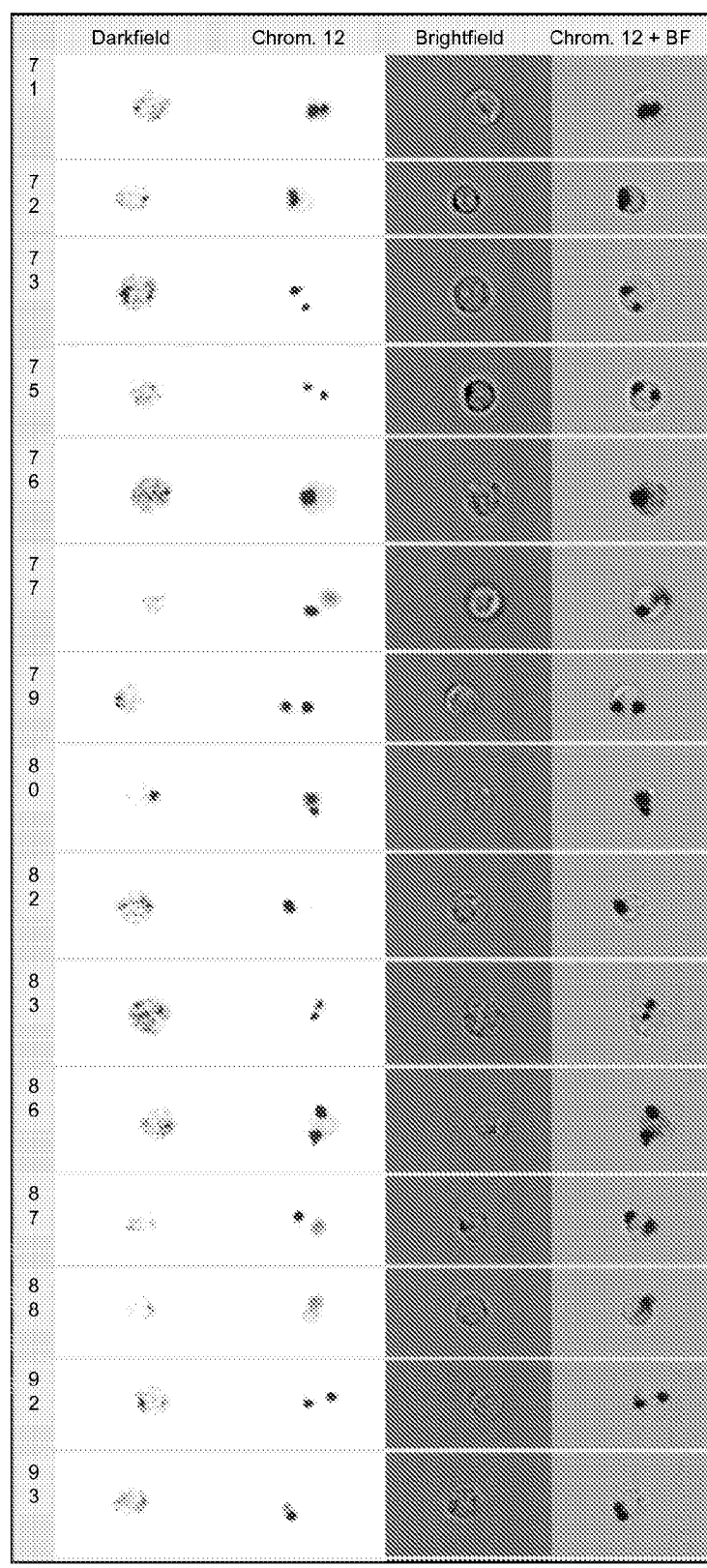
Figure 16:
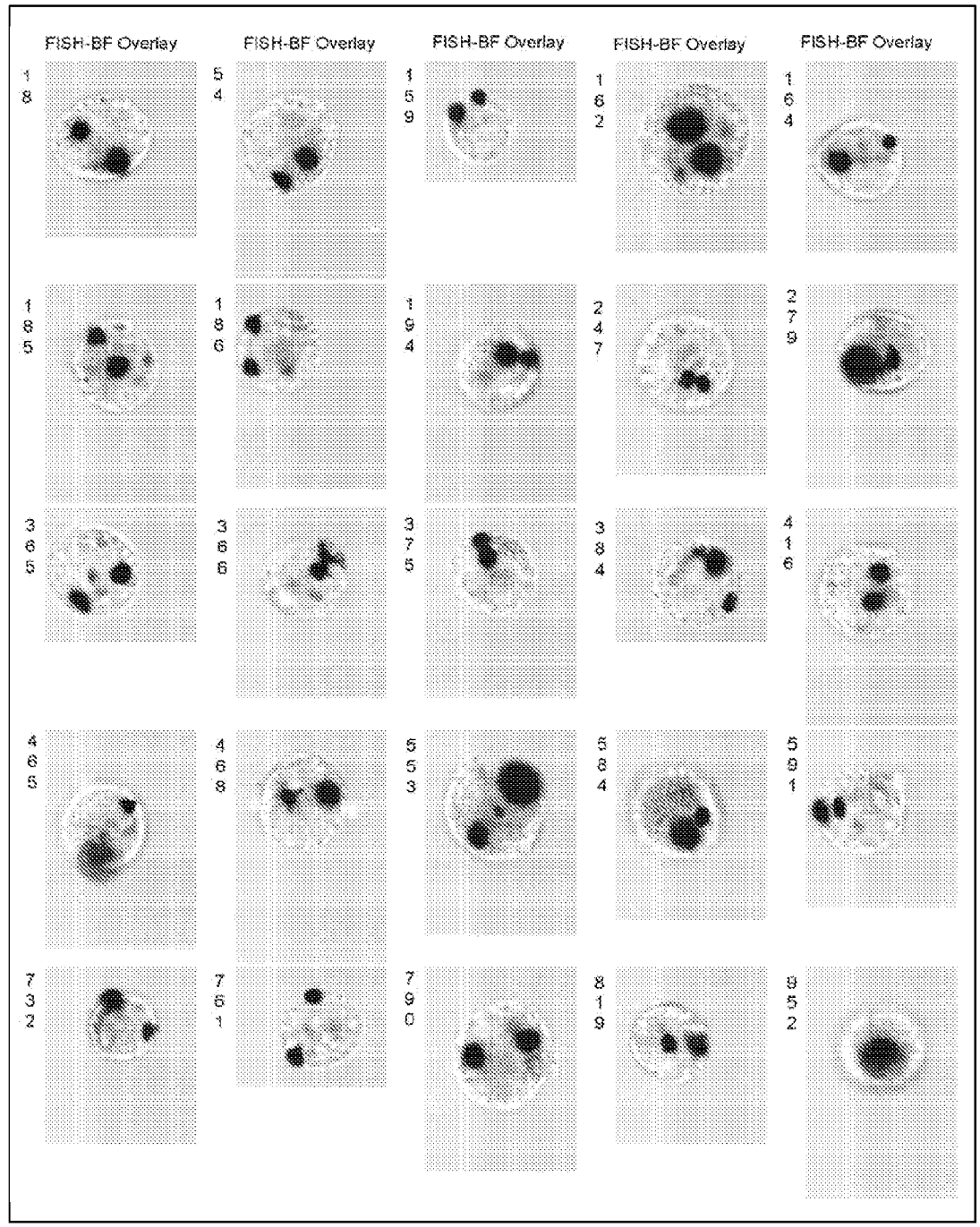
Figure 17:
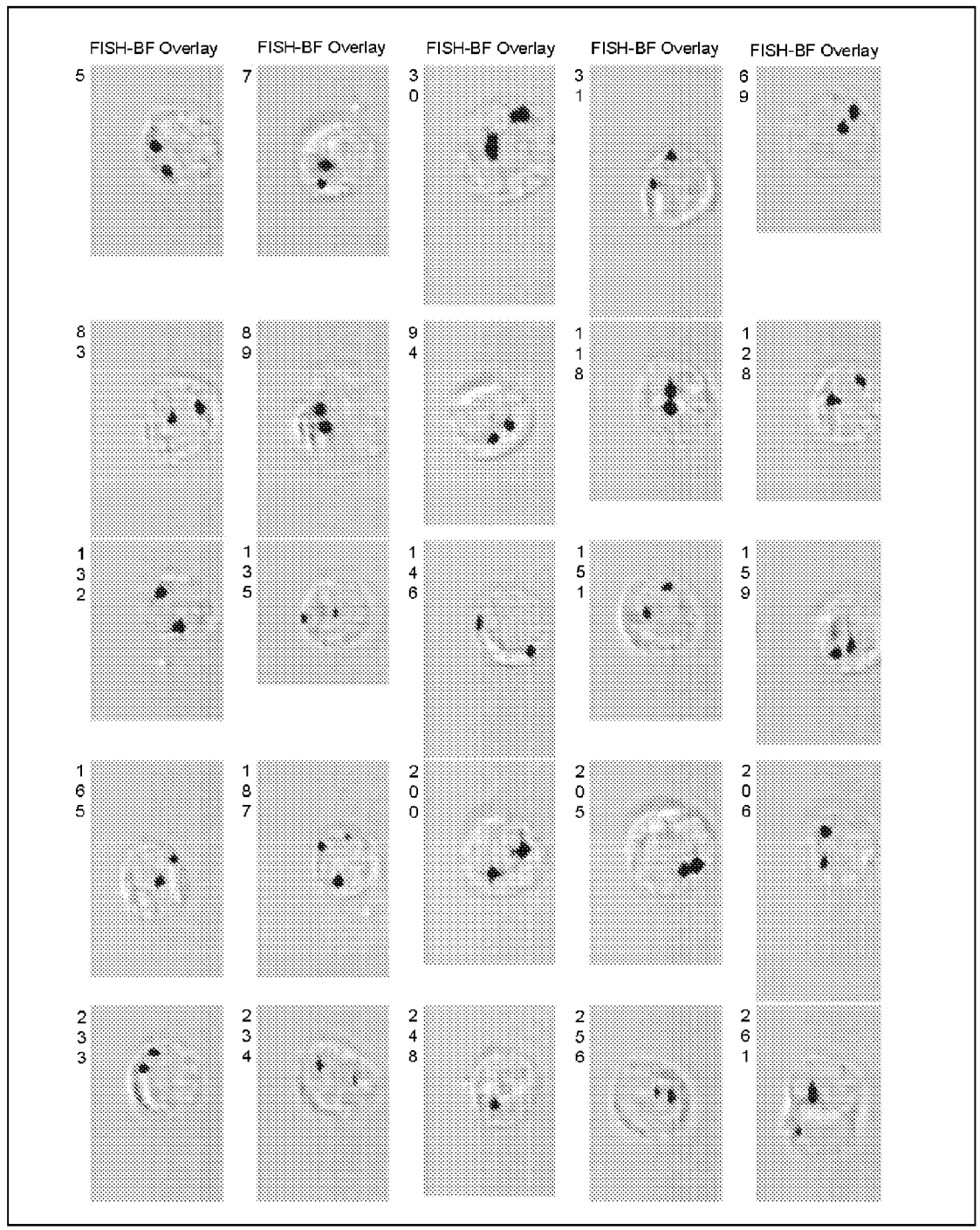

FIG. 6 includes images of normal (i.e., healthy) mammary epithelial cells;

FIG. 7 includes images of mammary carcinoma (i.e., diseased) cells, illustrating how quantification of data in a fluorescent channel serves as a marker for breast cancer;

FIG. 8A is an exemplary graphical user interface used to implement the method steps of FIG. 3;

FIGS. 8B-8M are histograms illustrating a plurality of different photometric and morphometric descriptors that can be used to automatically distinguish images of healthy mammary epithelial cells from images of mammary carcinoma cells;

FIG. 9 graphically illustrates the separation of cells in human peripheral blood into a variety of subpopulations based on photometric properties;

FIG. 10A graphically illustrates a distribution of normal peripheral blood mononuclear cells (PBMC) based on image data collected from a population of cells that do not include mammary carcinoma cells;

FIG. 10B graphically illustrates a distribution of normal PBMC and mammary carcinoma cells based on image data collected from a population of cells that includes both cell types, illustrating how the distribution of mammary carcinoma cells is distinguishable from the distribution of the normal PBMC cells;

FIG. 11A graphically illustrates a distribution of normal PBMC and mammary carcinoma cells based on measured cytoplasmic area derived from image data collected from a population of cells that includes both cell types, illustrating how the distribution of cytoplasmic area of the mammary carcinoma cells is distinguishable from the distribution of cytoplasmic area of the normal PBMC;

FIG. 11B graphically illustrates a distribution of normal PBMC and mammary carcinoma cells based on measured scatter frequency derived from image data collected from a population of cells that includes both cell types, illustrating how the distribution of the scatter frequency of the mammary carcinoma cells is distinguishable from the distribution of the scatter frequency of the normal PBMC;

FIG. 12 is composite images of cells generated by combining bright field and fluorescent images of mammary carcinoma cells;

FIG. 13 illustrates representative images of five different PBMC populations that can be defined by scatter data derived from image data of a population of cells;

FIG. 14 schematically illustrates an exemplary computing system used to implement the method steps of FIG. 3;

FIG. 15 is a grayscale representation of human PBMC hybridized in suspension with a chromosome 12 probe, where each cell is represented by a row of four images, from left to right including dark field (blue in a full color version of the image), fluorescence from a chromosome 12-SpectrumGreen probe (green in a full color version of the image), bright field (gray), and a superposition of the fluorescence and bright field images, in which an unbiased selection of cells illustrates variation in probe intensity, focus quality, and orientation with respect to the optic axis;

FIG. 16 is a grayscale representation of Jurkat cells hybridized in suspension with a chromosome 8 probe and imaged in flow using standard optics, wherein each cell is represented by a superposition of its chromosome 8 fluorescence (green in a full color version of the image) and bright field (gray) images; Jurkat cells are larger than human PBMC and exacerbate variations in image focus quality; and FIG. 17 is a grayscale representation of Jurkat cells hybridized in suspension with a chromosome 8 probe and imaged in flow using EDF optics, wherein each cell is represented by a superposition of its chromosome 8 fluorescence (green in a full color version of the image) and bright field (gray) images; EDF imaging greatly improves focus quality and the accuracy of FISH spot enumeration.

DESCRIPTION

Figures and Disclosed Embodiments Are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

With respect to the following disclosure, and the claims that follow, it should be understood that the term population of cells refers to a group of cells including a plurality of cells. Thus, a population of cells must include more than one cell.

The term cancer precursor is intended to refer to cell types that are abnormal but not cancerous.

The term multispectral images is intended to refer to images that are formed using light that has been spectrally dispersed (such as by a prism, where each different wavelength of light exits the prism at a different nominal angle) or spectrally decomposed (such as by a set of filters, where each filter emits a band of different wavelengths, such as red light, or blue light).

The term multimodal images is intended to refer to images that are formed using different types of light from a cell. Fluorescent images are formed using light emitted by the cell in response to the excitation of a fluorophore (naturally present or added to the cell). Dark field images and bright field images are formed using different illumination techniques, which are well known in the field of microscopy. Thus, fluorescent images, bright filed images, and dark field images each represent imaging modes. Multimodal images must therefore include at least two images acquired using a different mode.

The term morphometric parameter refers to a quantifiable parameter involving the shape of an object (i.e., a cell). Morphometrics facilitates rigorous comparisons, enables complex shapes to be described in a rigorous fashion, and permits numerical comparison between different shapes (i.e., cells). By reducing shape to a series of numbers, it allows objective comparisons. When applied to different types of cells on a statistical basis, morphometric analysis can highlight specific morphometric parameters that can be used to distinguish different types of cells.

The term photometric parameter refers to a quantifiable parameter that can be directly measured from an image, such as contrast, density, and color. Exemplary photometric parameters include, but are not limited to, nuclear optical density, cytoplasm optical density, background optical density, and ratios of selected pairs of these values.

Overview

The present disclosure encompasses a method of using flow imaging systems that can combine the speed, sample handling, and cell sorting capabilities of flow cytometry with the imagery, sensitivity, and resolution of multiple forms of microscopy and full visible/near infrared spectral analysis, to collect and analyze data relating to disease conditions in blood, particularly for detecting cancerous cells and precancerous cells.

A preferred imaging system to be used in collecting the image data required to implement the techniques disclosed herein will incorporate the following principal characteristics:
1. high speed measurement;
2. the ability to process very large or continuous samples;
3. high spectral resolution and bandwidth;
4. good spatial resolution;
5. high sensitivity; and
6. low measurement variation.

In particular, recently developed imaging flow cytometer technology, embodied in an instrument marketed under the name ImageStream™ by Amnis Corporation, Seattle Wash., provides each of the above-noted principle characteristics.

The ImageStream™ instrument is a commercial embodiment of the flow imaging system described below in detail with respect to FIG. 1A. Aspects of this imaging flow cytometer technology are described in the following commonly assigned patents: U.S. Pat. No. 6,249,341, issued on Jun. 19, 2001, entitled "Imaging And Analyzing Parameters of Small Moving Objects Such As Cells;" U.S. Pat. No. 6,211,955 issued on Apr. 3, 2001, also entitled "Imaging And Analyzing Parameters of Small Moving Objects Such As Cells;" U.S. Pat. No. 6,473,176, issued on Oct. 29, 2002, also entitled "Imaging And Analyzing Parameters of Small Moving Objects Such As Cells;" U.S. Pat. No. 6,583,865, issued on Jun. 24, 2003, entitled "Alternative Detector Configuration And Mode of Operation of A Time Delay Integration Particle Analyzer;" and U.S. patent application Ser. No. 09/989,031 entitled "Imaging And Analyzing Parameters of Small Moving Objects Such As Cells in Broad Flat Flow." While the ImageStream™ platform represents a particularly preferred imaging instrument used to acquire the image data that will be processed in accord with the concepts disclosed herein, it should be understood that the concepts disclosed herein are not limited only to the use of that specific instrument.

As noted above, in addition to collecting image data from a population of biological cells, an aspect of the concepts disclosed herein involves processing the image data collected to determine if any of the imaged cells in the population exhibit one or more characteristics associated with cancer or a precancerous condition. A preferred image analysis software package is IDEAS™ (Amnis Corporation, Seattle Wash.). The IDEAS™ package evaluates 250 features for every cell, including multiple morphologic and fluorescence intensity measurements, which can be used to define and characterize cell populations. The IDEAS™ package enables the user to define biologically relevant cell subpopulations, and analyze subpopulations using standard cytometry analyses, such as gating and backgating. It should be understood, however, that other image analysis methods or software packages can be implemented to apply the concepts disclosed herein, and the preferred image analysis software package that is disclosed is intended to be exemplary, rather than limiting of the concepts disclosed herein.

Overview of a Preferred Imaging System

Figure 1A:
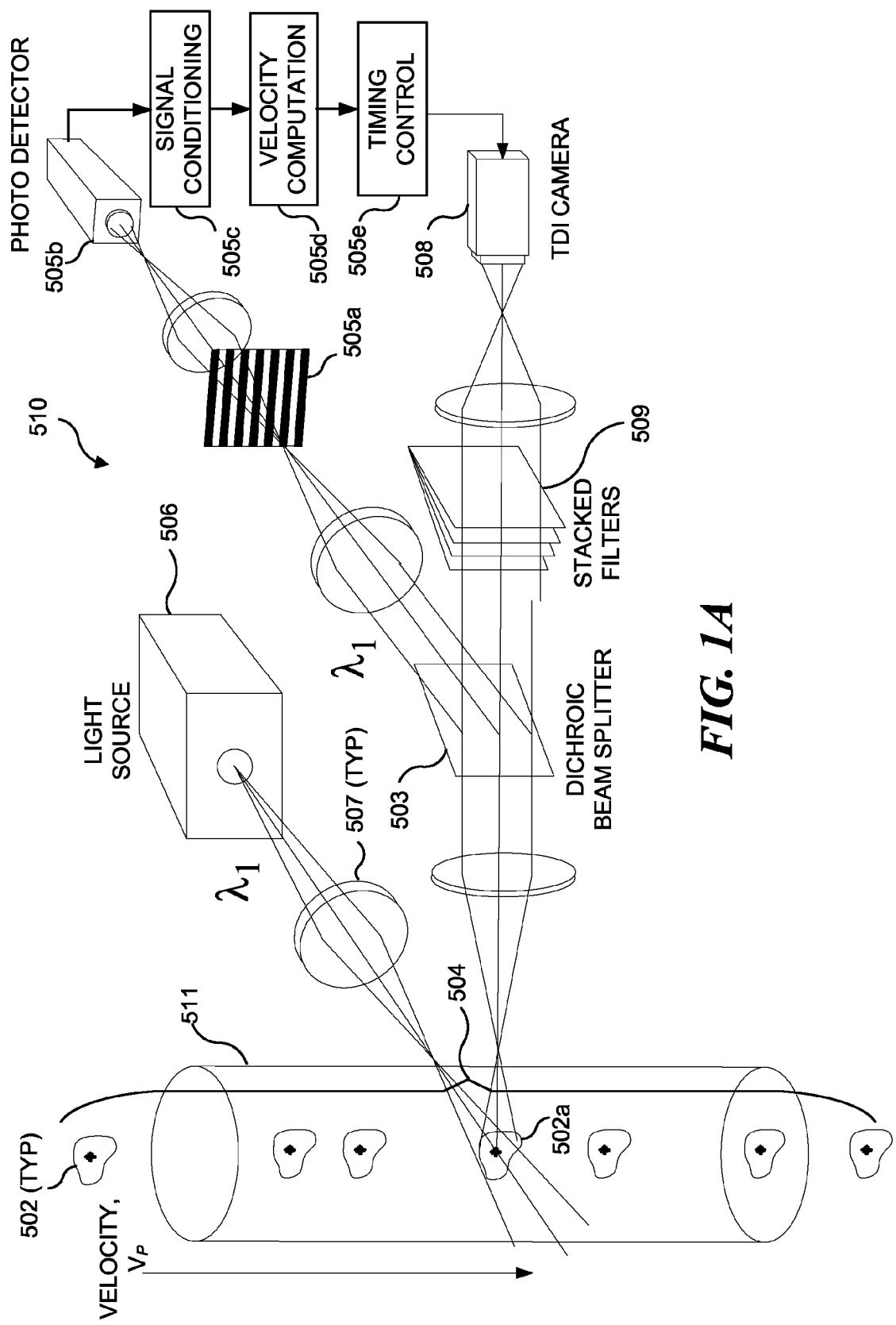
FIG. 1A is a schematic diagram of an exemplary flow imaging system that can be used to simultaneously collect a plurality of images from an object in flow.

FIG. 1A is a schematic diagram of a preferred flow imaging system 510 (functionally descriptive of the ImageStream™ platform) that uses TDI when capturing images of objects 502 (such as biological cells), entrained in a fluid flow 504. System 510 includes a velocity detecting subsystem that is used to synchronize a TDI imaging detector 508 with the flow of fluid through the system. Significantly, imaging system 510 is capable of simultaneously collecting a plurality of images of an object. A particularly preferred implementation of imaging system 510 is configured for multi-spectral imaging and can operate with six spectral channels: DAPI fluorescence (400-460 nm), Dark field (460-500 nm), FITC fluorescence (500-560 nm), PE fluorescence (560-595 nm), Bright field (595-650 nm), and Deep Red (650-700 nm). The TDI detector can provide 10 bit digital resolution per pixel. The numeric aperture of the preferred imaging system is typically 0.75, with a pixel size of approximately 0.5 microns. However, those skilled in the art will recognize that this flow imaging system is neither limited to six spectral channels, nor limited to either the stated aperture size or pixel size and resolution.

Moving objects 502 are illuminated using a light source 506. The light source may be a laser, a light emitting diode, a filament lamp, a gas discharge arc lamp, or other suitable light emitting source, and the system may include optical conditioning elements such as lenses, apertures, and filters that are employed to deliver broadband or one or more desired wavelengths or wavebands of light to the object with an intensity required for detection of the velocity and one or more other characteristics of the object. Light from the object is split into two light paths by a beam splitter 503. Light traveling along one of the light paths is directed to the velocity detector subsystem, and light traveling along the other light path is directed to TDI imaging detector 508. A plurality of lenses 507 are used to direct light along the paths in a desired direction, and to focus the light. Although not shown, a filter or a set of filters can be included to deliver to the velocity detection subsystem and/or TDI imaging detector 508, only a narrow band of wavelengths of the light corresponding to, for example, the wavelengths emitted by fluorescent or phosphorescent molecules in/on the object, or light having the wavelength(s) provided by the light source 506, so that light from undesired sources is substantially eliminated.

The velocity detector subsystem includes an optical grating 505a that amplitude modulates light from the object, a light sensitive detector 505b (such as a photomultiplier tube or a solid-state photodetector), a signal conditioning unit 505c, a velocity computation unit 505d, and a timing control unit 505e, which assures that TDI imaging detector 508 is synchronized to the flow of fluid 504 through the system. The optical grating preferably comprises a plurality of alternating transparent and opaque bars that modulate the light received from the object, producing modulated light having a frequency of modulation that corresponds to the velocity of the object from which the light was received. Preferably, the optical magnification and the ruling pitch of the optical grating are chosen such that the widths of the bars are approximately the size of the objects being illuminated. Thus, the light collected from cells or other objects is alternately blocked and transmitted through the ruling of the optical grating as the object traverses the interrogation region, i.e., the field of view. The modulated light is directed toward a light sensitive detector, producing a signal that can be analyzed by a processor to determine the velocity of the object. The velocity measurement subsystem is used to provide timing signals to TDI imaging detector 508.

Preferably, signal conditioning unit 505c comprises a programmable computing device, although an ASIC chip or a digital oscilloscope can also be used for this purpose. The frequency of the photodetector signal is measured, and the velocity of the object is computed as a function of that frequency. The velocity dependent signal is periodically delivered to a TDI detector timing control 505e to adjust the clock rate of TDI imaging detector 508. Those of ordinary skill in the art will recognize that the TDI detector clock rate is adjusted to match the velocity of the image of the object over the TDI detector to within a small tolerance selected to ensure that longitudinal image smearing in the output signal of the TDI detector is within acceptable limits. The velocity update rate must occur frequently enough to keep the clock frequency within the tolerance band as flow (object) velocity varies.

Beam splitter 503 has been employed to divert a portion of light from an object 502 to light sensitive detector 505b, and a portion of light from object 502a to TDI imaging detector 508. In the light path directed toward TDI imaging detector 508, there is a plurality of stacked dichroic filters 509, which separate light from object 502a into a plurality of wavelengths. One of lenses 507 is used to form an image of object 502a on TDI imaging detector 508.

The theory of operation of a TDI detector like that employed in system 510 is as follows. As objects travel through a flow tube 511 (FIG. 1A) and pass through the volume imaged by the TDI detector, light from the objects forms images of the objects, and these images travel across the face of the TDI detector. The TDI detector preferably comprises a charge coupled device (CCD) array, which is specially designed to allow charge to be transferred on each clock cycle, in a row-by-row format, so that a given line of charge remains locked to, or synchronized with, a line in the image. The row of charge is clocked out of the array and into a memory when it reaches the bottom of the array. The intensity of each line of the signal produced by the TDI detector corresponding to an image of an object is integrated over time as the image and corresponding resulting signal propagate over the CCD array. This technique greatly improves the signal-to-noise ratio of the TDI detector compared to non-integrating type detectors—a feature of great benefit in a detector intended to respond to images from low-level fluorescence emission of an object. Proper operation of the TDI detector requires that the charge signal be clocked across the CCD array in synchronization with the rate at which the image of the object moves across the CCD array. An accurate clock signal to facilitate this synchronization can be provided by determining the velocity of the object, and the concepts disclosed herein use an accurate estimate of the object's velocity, and thus, of the velocity of the image as it moves over the CCD array of the TDI detector. A flow imaging system of this type is disclosed in commonly assigned U.S. Pat. No. 6,249,341, the complete disclosure, specification, and drawings of which are hereby specifically incorporated herein by reference.

In a preferred implementation, cells are hydrodynamically focused into a single-file line in a fluidic system (not separately shown), forming a tall but narrow field of view. This technique enables the lateral dimension of the detector to be used for signal decomposition. This aspect of the preferred imaging system (i.e., ImageStream™) can be readily visualized in FIG. 1B. Cells 99 are hydrodynamically focused in a flow of fluid directed into a flow cuvette 116 and illuminated from one or more sides using light sources 98 and 100. Light is collected from the cells with a high NA objective lens 102, and the light that is collected is directed along a light path including lenses 103A and 103B, and a slit 105. A fraction of this collected light is transmitted to an auto-focus subsystem 104 and to a velocity detection system 106. It should be noted that in connection with an imaging system that uses a TDI detector, it is important to ensure the data signal produced by the detection system, which is integrated over time to increase the signal-to-noise ratio, is properly synchronized with the flow of cells through the imaging system.

Optional distortion elements can be included in the flow imaging system, to alter the optical wave front of light from the cells in a deterministic way. The combination of a modified wave front and post-processing of the imagery enables extended depth of field (EDF) images to be obtained by the imaging system. Either an optical distortion element 5A is disposed between the objects being imaged and the collection lens, or an optical distortion element 5B is disposed in infinite space (that is, at the objective aperture or at a conjugate image of the aperture at a subsequent location in the optical system, but before the detector). Alternatively, optical distortion may be introduced via adjustment of a correction collar on an adjustable implementation of objective lens 102. Only one means of introducing optical distortion is required. The function of the optical distortion is to change the light from the object to achieve a point spread function (PSF) that is substantially invariant across an EDF, such that negative effects of the distortion produced by the element can subsequently be removed by signal processing, to yield an EDF image.

Figure 1B:
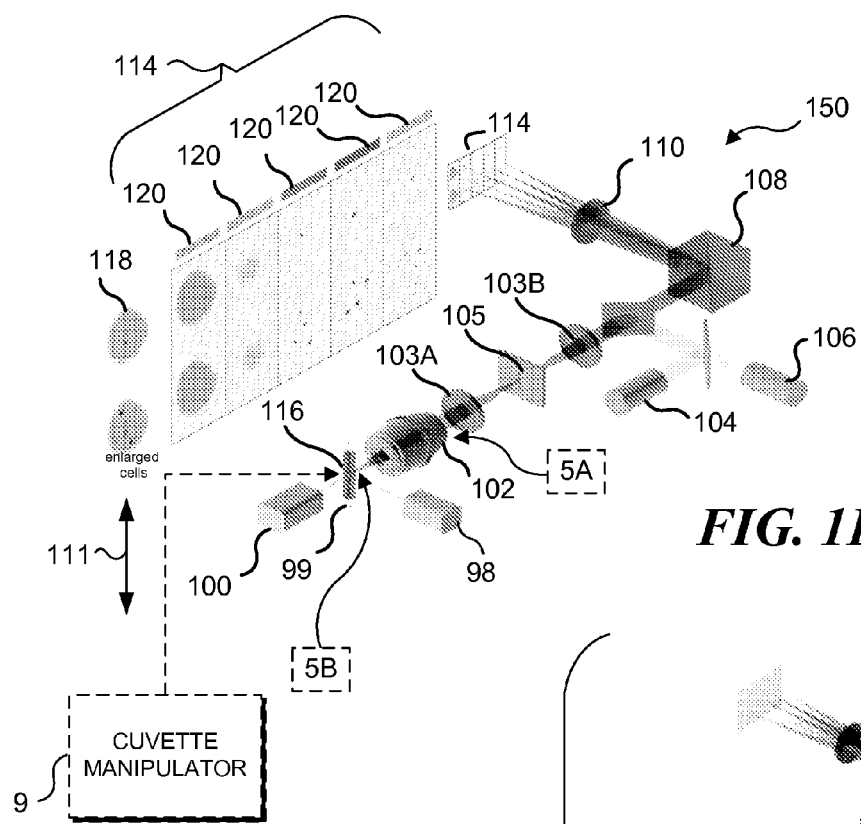
FIG. 1B is another illustration of an exemplary flow imaging system for implementing the concepts disclosed herein.

Another technique that can be used to introduce optical distortion into light from the object is to use a cuvette/flow cell having different optical thicknesses at different locations, such that imaging through the different locations of the cuvette induces different degrees of wave front deformation. For example, different faces of the cuvette can induce different levels of distortion, with one or more faces introducing no intentional distortion/deformation, with other faces configured to intentionally deform the optical wave front of light from the object. Moving the cuvette relative to the imaging optical system enables the deformation to be selectively induced. An optional cuvette manipulator 9 for manipulating the position of the cuvette relative to the optical system is shown in FIG. 1B. Where different faces of the cuvette induce different levels of deformation, such means will generally rotate the cuvette. It should also be recognized that a single face of a cuvette can induce different levels of deformation at different locations, such that translating the cuvette linearly can induce different levels of deformation. In such an embodiment, manipulator 9 will be configured to translate the cuvette linearly. Those of ordinary skill in the art will recognize that many different structural configurations can be used to implement manipulator 9, such as stepper motors, linear actuators, hydraulics, powered hinges, powered linkages, and others. The specific configuration is not critical, so long as manipulation of the cuvette does not introduce additional optical errors beyond the intentional deformation, thus the specified structures for manipulator 9 should be considered exemplary, rather than limiting.

The majority of the light is passed to a spectral decomposition element 108, which employs a fan-configuration of dichroic mirrors 110 to direct different spectral bands laterally onto different regions of a TDI detector 114. Thus, the imaging system is able to decompose the image of a single cell 118 into multiple sub-images 120 across detector 114, each sub-image corresponding to a different spectral component. In this view, detector 114 has been enlarged and is shown separately to highlight its elements. Note that the different spectral or sub images are dispersed across the detector orthogonally relative to a direction of motion of the images across the detector, as indicated by an arrow 111.

Figure 1C:
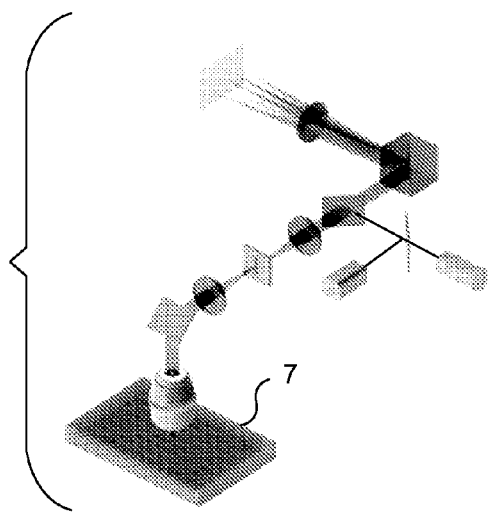
FIG. 1C is a schematic illustration of an exemplary imaging system for implementing the concepts disclosed herein, wherein the cells to be imaged are disposed on a plate or slide.

Spectral decomposition greatly facilitates the location, identification, and quantification of different fluorescence-labeled biomolecules within a cell by isolating probe signals from each other, and from background auto fluorescence. Spectral decomposition also enables simultaneous multi-mode imaging (bright field, dark field, etc.) using band-limited light in channels separate from those used for fluorescence imaging. FIG. 1B illustrates an exemplary flow-based embodiment of flow imaging system 150. However, it should be recognized that such an imaging system can be configured to collect images of objects on a plate or slide 7, where the plate/slide moves relative to the imaging system, instead of the flow-based embodiment, as indicated in FIG. 1C.

It should be recognized that other elements (such as a prism or a filter stack) could be similarly employed to spectrally disperse the light, and the dichroic mirrors simply represent an exemplary implementation. Flow imaging system 150 can employ a prism (not shown) or a grating oriented to disperse light laterally with regard to the axis of flow prior to the final focusing optics, for spectral analysis of each object's intrinsic fluorescence. In yet another exemplary embodiment of a suitable flow imaging system that is contemplated (but not shown), a cylindrical final focusing lens can be employed to image a Fourier plane on the detector in the cross-flow axis, enabling analysis of the light scatter angle. These techniques for multi-spectral imaging, flow spectroscopy, and Fourier plane scatter angle analysis can be employed simultaneously by splitting the collected light into separate collection paths, with appropriate optics in each light path. For enhanced morphology or to analyze forward scatter light, a second imaging objective and collection train can be used to image the particles through an orthogonal facet of the flow cuvette 116, thereby viewing the objects in stereoscopic perspective with no loss of speed or sensitivity.

To analyze the collected imagery, a software based image analysis program can be employed. One example of suitable image analysis software is the IDEAS™ package (available from Amnis Corporation, Seattle, Wash.). The IDEAS™ software package evaluates over 200 quantitative features for every cell, including multiple morphologic and fluorescence intensity measurements, which can be used to define and characterize cell populations. The IDEAS™ software package enables the user to define biologically relevant cell subpopulations, and analyze subpopulations using standard cytometry analyses, such as gating and backgating. It should be understood, however, that other image analysis methods or software packages can be employed to apply the concepts disclosed herein, and the IDEAS™ image analysis software package is intended to be merely one example of a suitable software for this purpose, rather than limiting on the concepts disclosed herein.

Figure 1D:
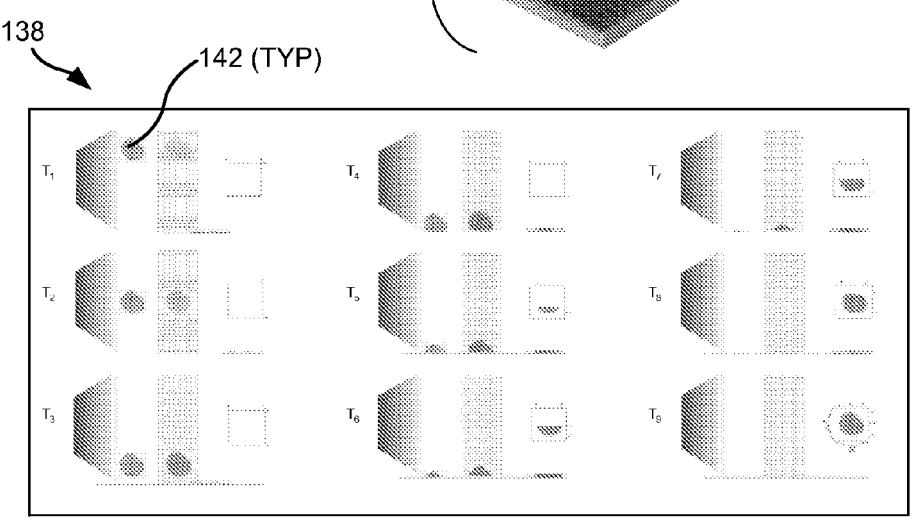
FIG. 1D is a schematic illustration of a readout provided by a TDI detector employed in an exemplary flow imaging system used in accord with the concepts disclosed herein.

Turning now to FIG. 1D, detector 114 of the exemplary flow imaging system shown in FIG. 1B is implemented using a TDI that performs high throughput imaging with high sensitivity. As shown in an exemplary readout 138, the image on the TDI detector is read out one row of pixels at a time from the bottom of the detector. After each row is read out, the signals in the remaining detector pixels are shifted down by one row. The readout/shift process repeats continuously, causing latent image 142 to translate down the detector during readout (note the movement of latent image 142 through frames T1-T6). If the readout rate of the TDI detector is matched to the velocity of the object being imaged, the image does not blur as it moves down the TDI detector. In effect, the TDI detector electronically "pans" the rate at which rows are read out to track the motion of an object being imaged. To provide optimum results for this technique, it is important to accurately measure the velocity of the objects being imaged and to employ that measurement in feedback control of the TDI readout rate. Thus, accurate velocity detection for objects moving in flow enables the TDI imaging to be implemented properly.

One primary advantage of TDI detection over other methods is the greatly increased image integration period it provides. An exemplary flow imaging system used in connection with the present invention includes a TDI detector that has 512 rows of pixels, provides a commensurate 512× increase in signal integration time. This increase enables the detection of even faint fluorescent probes within cell images and intrinsic auto fluorescence of cells acquired at a high-throughput.

Furthermore, the use of a TDI detector increases measured signal intensities up to a thousand fold, representing over a 30 fold improvement in the signal-to-noise ratio compared to other methods disclosed in the prior art. This increased signal intensity enables individual particles to be optically addressed, providing high-resolution measurement of either scattered spectral intensity of white light or scattered angular analysis of monochromatic light of selected wavelengths.

Exemplary flow imaging system 150 can be configured for multi-spectral imaging and can operate with, for example, six spectral channels: DAPI fluorescence (400-460 nm), Dark field (460-500 nm), FITC fluorescence (500-560 nm), PE fluorescence (560-595 nm), Bright field (595-650 nm), and Deep Red (650-700 nm). The TDI detector can provide 10 bit digital resolution per pixel. The NA of the exemplary imaging system is typically about 0.75, with a pixel size of approximately 0.5 microns. However, those skilled in the art will recognize that this flow imaging system is neither limited to six spectral channels nor limited to either the stated NA, or pixel size and resolution.

Figure 2:
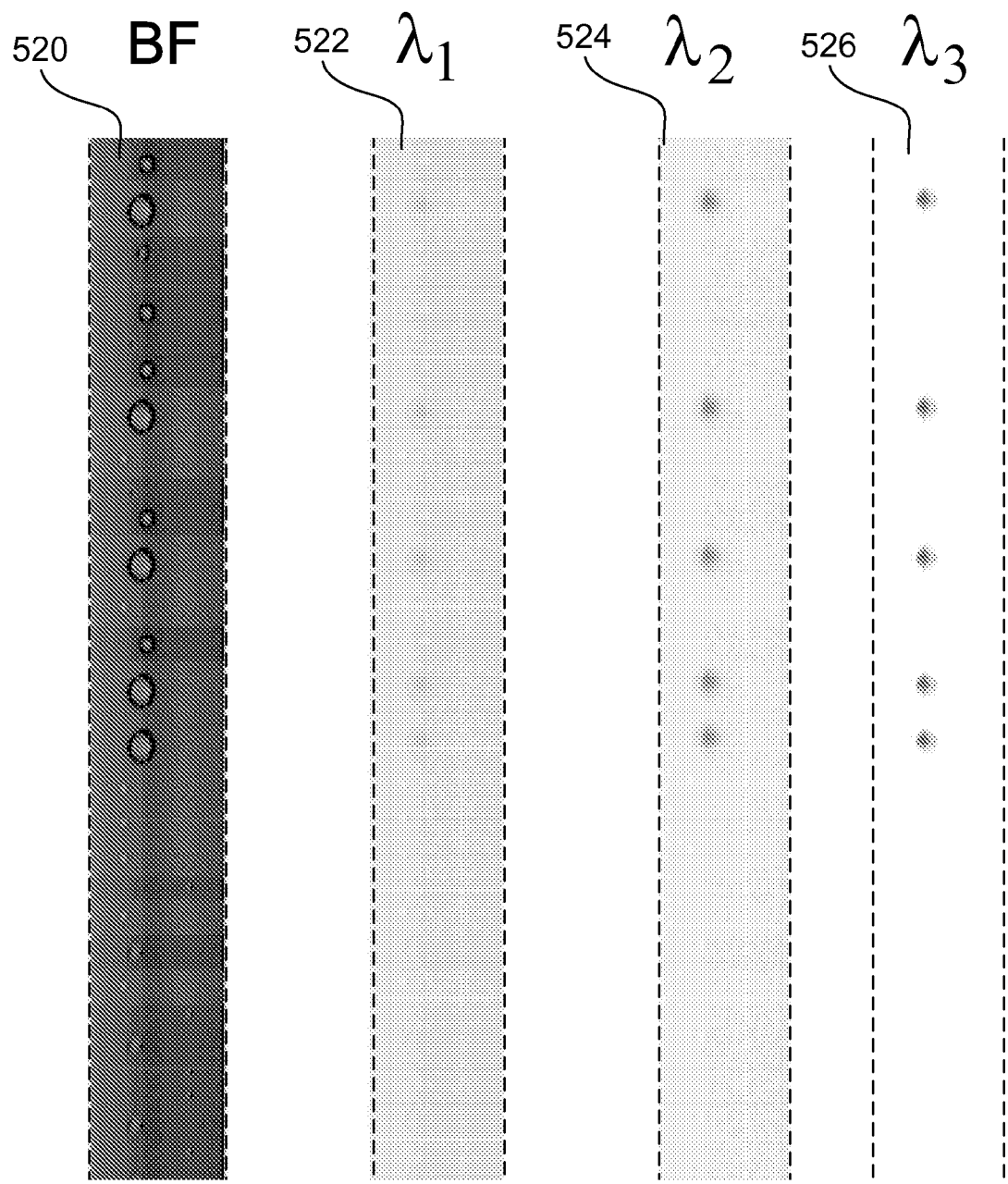
FIG. 2 is a pictorial representation of an image recorded by the flow imaging system of FIGS. 1A-1C.

FIG. 2 is a pictorial representation of images produced by the exemplary flow imaging systems of FIGS. 1A-1C. It should be recognized that while FIG. 2 is based on a full color image, that image has been manipulated to facilitate reproduction. The colors in the original image were reversed (i.e., a negative of the original image was obtained), then that negative was converted from a color image to a grayscale image, and contrast adjustments were performed. Thus, FIG. 2 is provided to indicate the types of cellular images that can be acquired, as opposed to faithfully reproducing actual cellular images in their original form. A column 520, labeled "BF," includes images created by the absorption of light from light source 506 by spherical objects 502 entrained in fluid flow 504. The "BF" label refers to "bright field," a term derived from a method for creating contrast in an image whereby light is passed through a region and the absorption of light by objects in the region produces dark areas in the image. The background field is thus bright, while the objects are dark in this image. Thus, column 520 is the "bright field channel." It should be understood that the inclusion of a bright field image is exemplary, rather than limiting on the scope of the concepts disclosed herein. Preferably, the concepts disclosed herein utilize a combination of bright field images and fluorescent images, or of dark field images and fluorescent images.

The remaining three columns 522, 524, and 526 shown in FIG. 2 are respectively labeled "$\lambda 1$," "$\lambda 2$," and "$\lambda 3$." These columns include images produced using light that has been emitted by an object entrained in the fluid flow. Preferably, such light is emitted through the process of fluorescence (as opposed to images produced using transmitted light). As those of ordinary skill in the art will recognize, fluorescence is the emission of light (or other electromagnetic radiation) by a substance that has been stimulated by the absorption of incident radiation. Generally, fluorescence persists only for as long as the stimulating radiation persists. Many substances (particularly fluorescent dyes) can be identified based on the spectrum of the light that is produced when they fluoresce. Columns 522, 524, and 526 are thus referred to as "fluorescence channels."

As noted above, additional exemplary flow imaging systems are disclosed in commonly assigned U.S. Pat. No. 6,211,955 and U.S. Pat. No. 6,608,682, the complete disclosure, specification, and drawings of which are hereby specifically incorporated herein by reference as background material. The imaging systems described above and in these two patents in detail, and incorporated herein by reference, have substantial advantages over more conventional systems employed for the acquisition of images of biological cell populations. These advantages arise from the use in several of the imaging systems of an optical dispersion system, in combination with a TDI detector that produces an output signal in response to the images of cells and other objects that are directed onto the TDI detector. Significantly, multiple images of a single object can be collected at one time. The image of each object can be spectrally decomposed to discriminate object features by absorption, scatter, reflection, or emissions, using a common TDI detector for the analysis. Other systems include a plurality of detectors, each dedicated to a single spectral channel.

These imaging systems can be employed to determine morphological, photometric, and spectral characteristics of cells and other objects by measuring optical signals including light scatter, reflection, absorption, fluorescence, phosphorescence, luminescence, etc. Morphological parameters include area, perimeter, texture or spatial frequency content, centroid position, shape (i.e., round, elliptical, barbell-shaped, etc.), volume, and ratios of selected pairs (or subsets) of these parameters. Similar parameters can also be determined for the nuclei, cytoplasm, or other sub-compartments of cells with the concepts disclosed herein. Photometric measurements with the preferred imaging system enable the determination of nuclear optical density, cytoplasm optical density, background optical density, and ratios of selected pairs of these values. An object being imaged with the concepts disclosed herein can either be stimulated into fluorescence or phosphorescence to emit light, or may be luminescent, producing light without stimulation. In each case, the light from the object is imaged on the TDI detector to use the concepts disclosed herein to determine the presence and amplitude of the emitted light, the number of discrete positions in a cell or other object from which the light signal(s) originate(s), the relative placement of the signal sources, and the color (wavelength or waveband) of the light emitted at each position in the object.

Using a Multispectral Imaging System to Analyze a Bodily Fluid for Cancer Cells

As noted above, aspects of the concepts disclosed herein involve both the collection of multispectral images from a population of biological cells, and the analysis of the collected images to identify at least one photometric or morphological feature that has been empirically determined to be associated with cancer cells or precancerous cells. Thus, an aspect of the present disclosure relates to the use of both photometric and morphometric features derived from multimode imagery of cells in flow to discriminate cell features in populations of cells, to facilitate the detection of the presence of cancer or a precancerous condition. Discussed in more detail below are methods for analyzing cells in suspension or flow, which may be combined with comprehensive multispectral imaging to provide morphometric and photometric data to enable, for example, the quantization of characteristics exhibited by both normal cells and cancer/precancerous cells, to facilitate the detection of cancer or abnormal cells indicative of a precancerous condition. Heretofore, such methods have not been feasible with standard microscopy and/or flow cytometry.

As noted above, a preferred flow imaging system (e.g., the ImageStream™ platform) can be used to simultaneously acquire multispectral images of cells in flow, to collect image data corresponding to bright field, dark field, and four channels of fluorescence. The ImageStream™ platform is a commercial embodiment based on the imaging systems described in detail above. In general, cells are hydrodynamically focused into a core stream and orthogonally illuminated for both dark field and fluorescence imaging. The cells are simultaneously trans-illuminated via a spectrally-limited source (e.g., filtered white light or a light emitting diode) for bright field imaging. Light is collected from the cells with an imaging objective lens and is projected on a CCD array. The optical system has a numeric aperture of 0.75 and the CCD pixel size in object space is $0.5\mu^2$, enabling high resolution imaging at event rates of approximately 100 cells per second. Each pixel is digitized with 10 bits of intensity resolution in this example, providing a minimum dynamic range of three decades per pixel. In practice, the spread of signals over multiple pixels results in an effective dynamic range that typically exceeds four decades per image. Additionally, the sensitivity of the CCD can be independently controlled for each multispectral image, resulting in a total of approximately six decades of dynamic range across all the images associated with an object. It should be understood that while the ImageStream™ platform represents a particularly preferred flow imaging system for acquiring image data in accord with the concepts disclosed herein, the ImageStream™ platform is intended to represent an exemplary imaging system, rather than limiting the concepts disclosed. Any imaging instrument capable of collecting images of a population of biological cells sufficient to enable the image analysis described in greater detail below to be achieved can be implemented in accord with the concepts presented herein.

Referring again to the preferred imaging system, the ImageStream™ platform, prior to projection on the CCD, the light is passed through a spectral decomposition optical system that directs different spectral bands to different lateral positions across the detector (such spectral decomposition is discussed in detail above in connection with the description of the various preferred embodiments of imaging systems). With this technique, an image is optically decomposed into a set of a plurality of sub-images (preferably 6 sub-images, including: bright field, dark field, and four different fluorescent images), each sub-image corresponding to a different spectral (i.e., color) component and spatially isolated from the remaining sub-images. This process facilitates identification and quantization of signals within the cell by physically separating on the detector signals that may originate from overlapping regions of the cell. Spectral decomposition also enables multimode imaging, i.e., the simultaneous detection of bright field, dark field, and multiple colors of fluorescence. The process of spectral decomposition occurs during the image formation process, rather than via digital image processing of a conventional composite image.

The CCD may be operated using TDI to preserve sensitivity and image quality even with fast relative movement between the detector and the objects being imaged. As with any CCD, image photons are converted to photo charges in an array of pixels. However, in TDI operation, the photo charges are continuously shifted from pixel to pixel down the detector, parallel to the axis of flow. If the photo charge shift rate is synchronized with the velocity of the image of the cell, the effect is similar to physically panning a camera. Image streaking is avoided despite signal integration times that are orders of magnitude longer than in conventional flow cytometry. For example, an instrument may operate at a continuous data rate of approximately 30 mega pixels per second and integrate signals from each object for 10 milliseconds, enabling the detection of even faint fluorescent probes within cell images to be acquired at relatively high speed. Careful attention to pump and fluidic system design to achieve highly laminar, non-pulsatile flow eliminates any cell rotation or lateral translation on the time scale of the imaging process (see, e.g., U.S. Pat. No. 6,532,061).

A real-time algorithm analyzes every pixel read from the CCD to detect the presence of object images and calculate a number of basic morphometric and photometric features, which can be used as criteria for data storage. Data files encompassing 10,000-20,000 cells are typically about 100 MB in size and, therefore, can be stored and analyzed using standard personal computers. The TDI readout process operates continuously without any "dead time," which means every cell can be imaged and the coincidental imaging of two or more cells at a time either in contact or not, presents no barrier to data acquisition.

Such an imaging system can be employed to determine morphological, photometric, and spectral characteristics of cells and other objects by measuring optical signals, including light scatter, reflection, absorption, fluorescence, phosphorescence, luminescence, etc. As used herein, morphological parameters (i.e., morphometrics) may be basic (e.g., nuclear shape) or may be complex (e.g., identifying cytoplasm size as the difference between cell size and nuclear size). For example, morphological parameters may include nuclear area, perimeter, texture or spatial frequency content, centroid position, shape (i.e., round, elliptical, barbell-shaped, etc.), volume, and ratios of selected pairs of these parameters. Morphological parameters of cells may also include cytoplasm size, texture or spatial frequency content, volume, and the like. As used herein, photometric measurements with the aforementioned imaging system can enable the determination of nuclear optical density, cytoplasm optical density, background optical density, and the ratios of selected pairs of these values. An object being imaged can be stimulated into fluorescence or phosphorescence to emit light, or may be luminescent, wherein light is produced by the object without stimulation. In each case, the light from the object may be imaged on a TDI detector of the imaging system to determine the presence and amplitude of the emitted light, the number of discrete positions in a cell or other object from which the light signal(s) originate(s), the relative placement of the signal sources, and the color (wavelength or waveband) of the light emitted at each position in the object.

The present disclosure provides methods of using both photometric and morphometric features derived from multi-mode imagery of cells in flow. Such methods can be employed as a cell analyzer to determine if a marker corresponding to a cancer cell or precancerous cell is present in the population of cells imaged. Preferably the population of cells is imaged while entrained in a fluid flowing through an imaging system. As used herein, gating refers to a subset of data relating to photometric or morphometric imaging. For example, a gate may be a numerical or graphical boundary of a subset of data that can be used to define the characteristics of particles to be further analyzed. Here, gates have been defined, for example, as a plot boundary that encompasses "in focus" cells, or sperm cells with tails, or sperm cells without tails, or cells other than sperm cells, or sperm cell aggregates, or cell debris. Further, backgating may be a subset of the subset data. For example, a forward scatter versus a side scatter plot in combination with a histogram from an additional marker may be used to backgate a subset of cells within the initial subset of cells.

Many of the applications of an imaging system as described herein will require that one or more light sources be used to provide light that is incident on the object being imaged. A person having ordinary skill in the art will know that the locations of the light sources substantially affect the interaction of the incident light with the object and the kind of information that can be obtained from the images using a detector.

In addition to imaging an object with the light that is incident on it, a light source can also be used to stimulate emission of light from the object. For example, a cell having been contacted with a probe conjugated to a fluorochrome (e.g., such as FITC, PE, APC, Cy3, Cy5, or Cy5.5) will fluoresce when excited by light, producing a corresponding characteristic emission spectra from any excited fluorochrome probe that can be imaged on a TDI detector. Light sources may alternatively be used for causing the excitation of fluorochrome probes on an object, enabling a TDI detector to image fluorescent spots produced by the probes on the TDI detector at different locations as a result of the spectral dispersion of the light from the object that is provided by a prism. The disposition of these fluorescent spots on the TDI detector surface will depend upon their emission spectra and their location in the object.

Each light source may produce light that can either be coherent, non-coherent, broadband, or narrowband light, depending upon the application of the imaging system desired. Thus, a tungsten filament light source can be used for applications in which a narrowband light source is not required. For applications such as stimulating the emission of fluorescence from probes, narrowband laser light is preferred, since it also enables a spectrally decomposed, non-distorted image of the object to be produced from light scattered by the object. This scattered light image will be separately resolved from the fluorescent spots produced on a TDI detector, so long as the emission spectra of any of the spots are at different wavelengths than the wavelength of the laser light. The light source can be either of the continuous wave (CW) or pulsed type, such as a pulsed laser. If a pulsed type illumination source is employed, the extended integration period associated with TDI detection can enable the integration of signals from multiple pulses. Furthermore, it is not necessary for the light to be pulsed in synchronization with the TDI detector.

Particularly for use in collecting image data for cell populations found in bodily fluids such as blood, it can be desirable to employ a 360 nm UV laser as a light source, and to optimize the optical system of the imaging system for diffraction-limited imaging performance in the 400-460 nm (DAPI emission) spectral band. In embodiments consistent with the disclosure herein, it is to be understood that relative movement exists between the object being imaged and the imaging system. In most cases, it will be more convenient to move the object than to move the imaging system. It is also contemplated that in some cases, the object may remain stationary and the imaging system move relative to it. As a further alternative, both the imaging system and the object may be in motion, which movement may be in different directions and/or at different rates.

Exemplary High Level Method Steps

FIG. 3 is a flow chart 400 schematically illustrating exemplary steps that can be used to detect cancer (or a precancerous condition) by analyzing a population of cells collected from a bodily fluid (such as blood), based on images of the cell population. First, one or more markers or characteristics that can be measured from images collected by the imaging system used to image the population of cells must be correlated to cancer cells (or precancerous cells). Once such a marker has been identified, a sample of bodily fluid from a patient can be very rapidly and easily analyzed to determine if that sample includes any cells having the identified marker.

In a block 402, an imaging system, such as the exemplary imaging systems described above in detail, is used to collect image data from a first population of biological cells where cancer or a precancerous condition is known to be present.

In a block 404, the imaging system is used to collect image data from a second population of biological cells, where the cell population includes only normal, healthy cells. If either the healthy cells or the cancerous/precancerous cells are fluorescently labeled, the first and second cell populations can be combined and imaged together.

In a block 406 at least one photometric or morphometric marker associated with the cancerous condition is identified. The marker relates to identifying a photometric and/or morphometric difference between healthy cells and cancerous/precancerous cells. As will be described in greater detail below, such markers include differences in the average nucleus size between healthy cells and carcinoma cells, and differences in images of healthy cells and carcinoma cells. These differences can be quantified based on processing the image data for the population of cells, to identify images that are more likely to be images of carcinoma cells, and to identify images that are more likely to be images of healthy cells.

Once a photometric and/or morphometric marker associated with the cancerous condition is identified, image data are collected from a sample of a bodily fluid acquired from a patient, where it is not known whether or not the patient has cancer. In a block 408 a sample of bodily fluid from a patient is obtained. In a block 410 image data are collected for the sample, and then the image data are analyzed in a block 412 for the presence of the previously identified marker, to determine whether cancer or a precancerous condition is present in the sample from the patient.

It should be noted that different types of cancer will likely exhibit different markers, thus the steps of blocks 402 and 406 will likely be repeated to identify markers for different types of cancer cells. Populations of abnormal cells that are not cancerous, but which may be indicative of a precancerous condition (i.e., neoplastic cells) can also be imaged to identify similar markers. Benign neoplastic cell masses include uterine fibroids and skin moles. These types of neoplastic cells do not transform into cancer. Potentially malignant neoplasms include carcinoma in situ. Given time, these neoplastic cell types will likely transform into a cancer, and thus are indicative of a precancerous condition (malignant neoplasms are commonly referred to as cancer; and invade and destroy the surrounding tissue and may metastasize). Thus, the steps of blocks 402 and 406 may also be optimized to identify markers to look for potentially malignant neoplastic cells, in addition to cancer cells.

While not strictly required, in a working embodiment of the techniques described herein, additional processing was implemented to reduce crosstalk and spatial resolution for the multi-channel imaging. The crosstalk reduction processing implemented is described in commonly assigned U.S. Pat. No. 6,763,149, the specification, disclosure and the drawings of which are hereby specifically incorporated herein by reference as background material. Those of ordinary skill in the art will recognize that other types of crosstalk reduction techniques could alternatively be implemented.

Identification of Exemplary Photometric and Morphometric Cancer Markers

In the context of the present disclosure, the multi-spectral imaging flow cytometer described above employs UV excitation capabilities and algorithms to quantitate DNA content and nuclear morphology, for the purpose of identifying and detecting cancerous and precancerous cells. In addition to employing a flow imaging instrument including a 360 nm UV laser and an optical system optimized for diffraction-limited imaging performance in the 400-460 nm (DAPI emission) spectral band, an imaging processing system is employed to process the image data. A personal computer executing image processing software represents an exemplary imaging processing system. The imaging processing software incorporates algorithms enabling photometric and/or morphometric properties of cells to be determined based on images of the cells. Exemplary algorithms include masking algorithms, algorithms that define nuclear morphology, algorithms for the quantization of cell cycle histograms, algorithms for analyzing DNA content, algorithms for analyzing heterochromaticity, algorithms for analyzing N/C ratio, algorithms for analyzing granularity, algorithms for analyzing CD45 expression, and algorithms for analyzing other parameters. In addition, the imaging processing software incorporates an algorithm referred to as a classifier, a software based analysis tool that is configured to evaluate a sample population of cells to determine if any disease condition markers are present. For determining the presence of cancer cells, the classifier will analyze the images of the sample population for images having photometric and/or morphometric properties corresponding to previously identified photometric and/or morphometric properties associated with cancer cells.

Significantly, for detection of epithelial cell carcinomas, high rates of data acquisition is required. Such cells have been reported to range from 1 cell in 100,000 peripheral blood leukocytes to 1 cell in 1,000,000 peripheral blood leukocytes. The ImageStream™ cytometer and IDEAS™ analytical software package discussed above are ideally suited for this application. Imagery from peripheral blood leukocytes can be obtained in the absence of artifacts typical of preparing blood films. Large cell numbers (in the tens and hundreds of thousands) can be accumulated per sample, providing greater confidence in the analysis of subpopulations. Immunofluorescent staining with accepted markers (CD5, CDI9, etc.) can easily be correlated with morphology. The quantitative cell classifiers eliminate the subjectivity of human evaluation, giving comparisons between patients a degree of confidence previously unattainable. Longitudinal studies will also benefit greatly by the quantitative analysis, and the ability to digitally store and retrieve large numbers of cellular image files, particularly as compared to prior art techniques for the retrieval of microscope slides and/or digital photographs of relatively small numbers of cells.

Discrimination of Morphological Features Using Fluorescence-Based Methodologies

A technology employed in detection of cancer cells in a bodily fluid based on image data of a population of cells from the bodily fluid was the development of preliminary absorbance and fluorescence staining protocols for simultaneous morphological analysis of bright field and fluorescence imagery.

Initially, investigations considered the simultaneous use of chromogenic stains and fluorescent dyes. The ability of the imaging system discussed above to produce bright field imagery, as well as multiple colors of fluorescence imagery of each cell, raised the possibility of simultaneously employing both traditional chromogenic stains and fluorescent dyes for analysis. However, because chromogenic stains do not normally penetrate cell membranes of viable cells, and because the optical systems discussed above are able to collect laser side scatter imagery, it was determined that much of the information on cell granularity that was traditionally acquired via stains, such as Eosin, could be obtained using laser side scatter imagery, without the need for cell staining. Numerous cell-permeant fluorescent dyes offer nuclear morphology without the need for fixing and chromogenic staining. Based on these considerations, it was determined that fluorescence-based alternatives for discrimination of morphological features provide a better approach than traditional staining methodologies.

The primary fluorescence-based alternatives to chromogenic stains useful in conjunction with the optical systems discussed above are fluorescent DNA binding dyes. A wide variety of such dyes are excitable at 488 nm, including several SYTO dyes (Molecular Probes), DRAQ5 (BioStatus), 7-AAD, Propidium Iodide (PI), and others. These dyes are alternatives to chromogenic nuclear stains such as Toluidine Blue, Methyl Green, Crystal Violet, Nuclear Fast Red, Carmalum, Celestine Blue, and Hematoxylin. A fluorescent DNA binding dye is generally included in assay protocols developed for use with the optical systems described above, for the purposes of defining the shape and boundaries of the nucleus, its area, its texture (analogous to heterochromaticity), as well as to provide DNA content information.

Figure 4:
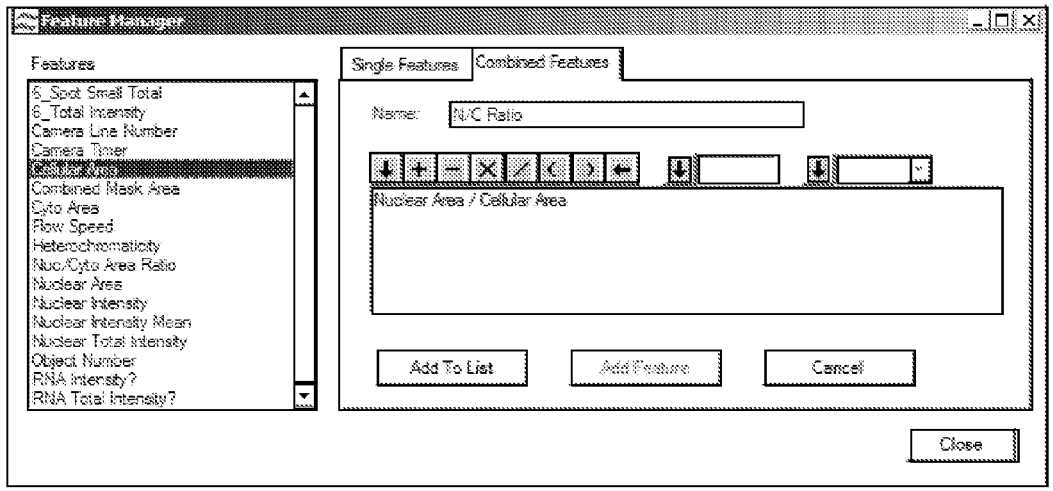
FIG. 4 is an exemplary graphical user interface used to implement the method steps of FIG. 3.

IDEAS™, the software image analysis program discussed above, enables evaluation of combinations of features from different images of the same cell, in order to expand the utility of the fluorescence nuclear image. For example, the nuclear image mask can be subtracted from the bright field image mask (which covers the entire cell) as a means for generating a mask that includes only the cytoplasmic region. Once defined, the cytoplasmic mask can be used to calculate the cytoplasmic area, the N/C ratio, the relative fluorescence intensity of probes in the cytoplasm and nucleus, etc., via an intuitive "Feature Manager." An example of a Feature Manager session for the definition of the N/C ratio is shown in FIG. 4. Basic features associated with any cell image are selected from a list and combined algebraically using a simple expression builder.

Measurement of Photometric and Morphometric Parameters

Figure 5:
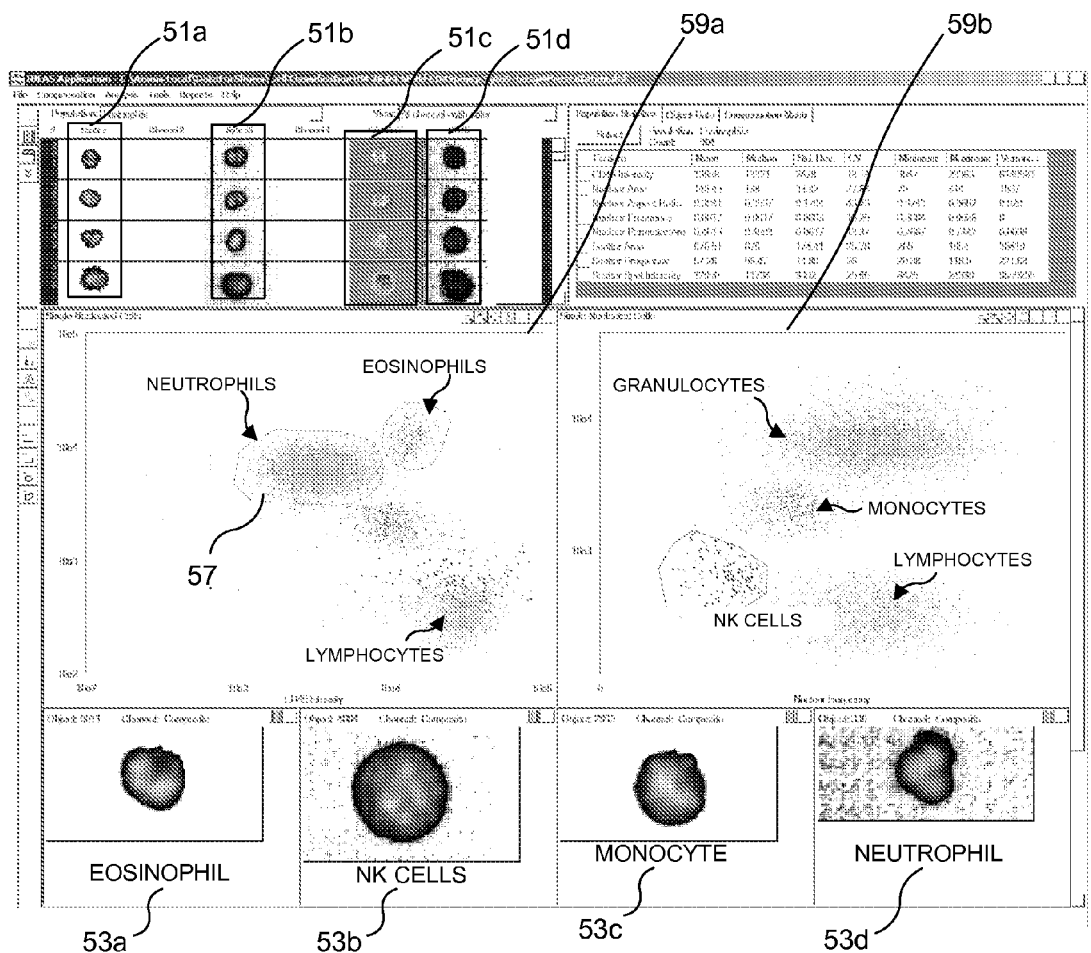
FIG. 5 is an exemplary graphical user interface used to implement the method steps of FIG. 3 as applied to the analysis of human peripheral blood.

In an exemplary implementation of the concepts disclosed herein, ImageStream™ data analysis and cell classification are performed post-acquisition using the IDEAS™ software package. An annotated IDEAS™ software screen capture of an analysis of human peripheral blood is shown in FIG. 5. The IDEAS™ software enables the visualization and photometric/morphometric analysis of data files containing imagery from tens of thousands of cells, thereby combining quantitative image analysis with the statistical power of flow cytometry.

The exemplary screen shot of FIG. 5 includes images and quantitative data from 20,000 human peripheral blood mononuclear cells. Whole blood was treated with an erythrocyte lysing agent, and the cells were labeled with an anti-CD45-PerCP mAb (red) and a DNA binding dye (green). Each cell was imaged in fluorescence using the FL1 and FL4 spectral bands, as well as dark field and bright field. Images of a plurality of cells in a dark field channel 51a, a green fluorescent channel 51b, a bright field channel 51c, and a red fluorescent channel 51d can readily be identified in this Figure. Such a thumbnail image gallery (in the upper left of the interface) enables the "list mode" inspection of any population of cells. Cell imagery can be pseudo-colored and superimposed for visualization in the image gallery or enlarged, as shown at the bottom of the interface, for four different cell types (eosinophils 53a, NK cells 53b, monocytes 53c, and neutrophils 53d).

The software also enables one- and two-dimensional plotting of features calculated from the imagery. Dots 55 that represent cells in the two-dimensional plots can be "clicked" to view the associated imagery in the gallery. The reverse is true as well. Cell imagery can be selected to highlight the corresponding dot in every plot in which that cell appears. In addition, gates 57 can be drawn on the plots to define subpopulations, which can then be inspected in the gallery using a "virtual cell sort" functionality. Any feature calculated from the imagery or defined by the user (i.e., selected from a list of basic and automatically combined algebraically using a simple expression builder) can be plotted. A dot plot 59a (displayed at the center left of FIG. 5) shows the clustering resulting from an analysis of CD45 expression (x-axis) versus a dark field granularity metric (y-axis), which is similar to side-scatter intensity measured in conventional flow cytometry. Plot 59a reveals lymphocytes (green in a full color image), monocytes (red in a full color image), neutrophils (turquoise in a full color image), and eosinophils (orange in a full color image). A dot plot 59b (displayed at the center right of FIG. 5) substitutes a nuclear texture parameter, "nuclear frequency" for CD45 expression on the x-axis, revealing a putative NK cell population (purple in a full color image). Back-displaying the purple population on the left dot plot reveals that this population has the same mean CD45 expression as the lymphocyte population (green on a full color image). The frequency parameter is one member of the morphologic and photometric feature set that was developed and incorporated into the IDEAS™ software package. Table 1 below provides an exemplary listing of photometric and morphometric definitions that can be identified for every image (or subpopulation, as appropriate). It should be recognized that FIG. 5 has been modified to facilitate its reproduction. As a full-color image, the background of each frame including a cell is black, and the background for each dot plot is black, to facilitate visualization of the cells and data.

TABLE 1

Morphometric and Photometric Definitions

| Image Features | Description of Parameters for Each Image (6 per object) |
|---|---|
| Area | Area of mask in pixels |
| Aspect Ratio | Aspect ratio of mask |
| Aspect Ratio Intensity | Intensity-weighted aspect ratio of mask |
| Background Mean Intensity | Mean intensity of pixels outside of mask |
| Background StdDev Intensity | Standard deviation of intensity of pixels outside of mask |
| Centroid X | Centroid of mask in horizontal axis |
| Centmid X Intensity | Intensity-weighted centroid of mask in horizontal axis |
| Centroid Y | Centroid of mask in vertical axis |
| Centmid Y Intensity | Intensity-weighted centroid of mask in vertical axis |
| Combined Mask Intensity | Total intensity of image using logical "OR" of all six image masks |
| Frequency | Variance of intensity of pixels within mask |
| Gradient Max | Maximum intensity gradient of pixels within mask |
| Gradient RMS | RMS of intensity gradient of pixels within mask |
| Intensity | Background-corrected sum of pixel intensities within mask |
| Major Axis | Major axis of mask in pixels |
| Major Axis Intensity | Intensity-weighted major axis of mask in pixels |
| Mean Intensity | Total Intensity of image divided by area of mask |
| Minimum Intensity | Minimum pixel intensity within mask |
| Minor Axis | Minor axis of mask in pixels |
| Minor Axis Intensity | Intensity-weighted minor axis of mask in pixels |
| Object Rotation Angle | Angle of major axis relative to axis of flow |
| Object Rotation Angle Intensity | Angle of intensity-weighted major axis relative to axis of flow |
| Peak Intensity | Maximum pixel intensity within mask |
| Perimeter | Number of edge pixels in mask |
| Spot Large Max | Maximum pixel intensity within large bright spots |
| Spot Large Total | Sum of pixel intensities within large bright spots |
| Spot Medium Max | Maximum pixel intensity within medium-sized bright spots |
| Spot Medium Total | Sum of pixel intensities within medium-sized bright spots |
| Spot Raw Max | Un-normalized maximum pixel intensity within large bright spots |
| Spot Raw Total | Sum of un-normalized pixel intensities within large bright spots |
| Spot Small Max | Maximum pixel intensity within small bright spots |
| Spot Small Total | Sum of pixel intensities within small bright spots |
| Total Intensity | Sum of pixel intensities within mask |
| Spot Count | Number of spots detected in image |
| Combined Mask Area | Area of logical 'OR' of all six image masks in pixels |
| Flow Speed | Camera line readout rate in Hertz at time object was imaged |

TABLE 1-continued

Morphometric and Photometric Definitions

| Image Features | Description of Parameters for Each Image (6 per object) |
|---|---|
| Object Number | Unique object number |
| Similarity | Pixel intensity correlation between two images of the same object |
| User-Defined Features | Any algebraic combination of imagery and masks |
| User-Defined Masks | Erode, dilate, threshold, Boolean combinations |
| User-Defined Populations | Any Boolean combination of defined populations |

Features that quantitate morphology are shown in italics in Table 1. Each feature is automatically calculated for all six types of images (dark field, bright field, and four fluorescent images, that are simultaneously captured) for each cell, when an image data set is loaded into the software.

Over 35 features are calculated per image, which amounts to over 200 features per cell in assays that employ all six images, not including user-defined features. Each cell is also assigned a unique serial number and time stamp, enabling kinetic studies over cell populations.

Selection of a Photometric/Morphometric Marker for Carcinoma Cells

It was initially proposed that bladder epithelial cells would be used to investigate morphometric differences between normal and epithelial carcinoma cells. However, the initial samples of bladder washings that were analyzed revealed that the cell number per sample was highly variable, and generally too low to be practical for use in the ImageStream™ instrument. Mammary epithelial cells were therefore used in place of bladder cells. Mammary cells were chosen because normal, primary cells of this kind are commercially available (Clonetics/InVitrogen) and will expand as adherent cells in short-term tissue culture with specialized growth media. In addition, mammary epithelial carcinoma cells derived from breast cancer metastases are available from the American Type Tissue Culture Collection (ATCC). In order to better control for tumor to tumor variability, three different mammary epithelial carcinoma cell lines were studied: HCC-1 500, HCC-1 569, and HCC-1428. These lines were established from metastases in three separate patients and were purchased from ATCC as frozen stocks. The cell lines grew adherent to plastic, were expanded by routine tissue culture methods, and used experimentally.

Normal and cancerous mammary epithelial cells were harvested separately by brief incubation with trypsin/EDTA at 37 degrees Celsius. The cells were washed once in cold phosphate buffer solution (PBS) containing 1% FCS, counted, and used experimentally. The three separate mammary epithelial carcinoma cell lines were pooled in equal proportions for the experiments described below.

Normal mammary epithelial cells were stained with a fluorescein-conjugated monoclonal antibody to the HLA Class I MHC cell surface protein by incubating the cells with the appropriate, predetermined dilution of the mAb for 30 minutes at 4 degrees C. Despite the fact that mammary carcinomas are known to down-regulate Class I MHC expression, as a precaution, the normal cells were fixed in 1% paraformaldehyde to limit passive transfer to the carcinoma cells. The combined mammary carcinoma cells lines were also fixed in 1% paraformaldehyde and added to the normal mammary cell population. DRAQ5 (BioStatus, Ltd, Leicestershire, UK), a DNA binding dye that can be excited with a 488 nm laser and emits in the red waveband, was added to the sample prior to running on the ImageStream™ instrument. The labeling of normal mammary epithelial cells with anti-Class I MHC mAb enabled the normal cells to be identified in mixes of normal and carcinoma cells, thereby providing an objective "truth" to facilitate the identification of image features distinguishing normal epithelial cells from epithelial carcinoma cells.

Mammary carcinomas are known to down-regulate class I MHC expression, but, as a precaution against passive transfer of antibody to the carcinoma cells, the normal and pooled carcinoma cells were fixed separately in 1% paraformaldehyde before mixing. DRAQ5, a DNA-binding dye that can be excited with a 488-nm laser and emits in the red waveband (BioStatus, Leicestershire, United Kingdom), was added to the sample before running on the ImageStream™, providing DNA content and nuclear morphology features for the analysis.

Image files containing image data of normal mammary epithelial cells mixed with mammary carcinoma cells were analyzed using the IDEAS™ software package with the results described below.

After performing spectral compensation on the data file, an initial visual inspection was performed to compare normal mammary epithelial cells (positive for class I HLA) to the unstained carcinoma cells. Representative images of normal cells are shown in FIG. 6 and representative carcinoma cells are shown in FIG. 7. Both figures present each cell as a row of pseudo-colored images in six channels (left to right): channel 1-blue laser side scatter (dark field); channel 2-blank; channel 3-green HLA-fluorescein-5-isothiocyanate (FITC) fluorescence; channel 4-blank; channel 5-bright field imagery; and channel 6-red nuclear fluorescence. It must be noted that while FIGS. 6 and 7 are based on full color images, those images have been manipulated to facilitate reproduction. The colors in the original images have been reversed (i.e., a negative of the original image was obtained), then that negative was converted from a color image to a grayscale image, and contrast adjustments were performed. Thus, FIGS. 6 and 7 are provided to indicate the types of cellular images that can be acquired, as opposed to faithfully reproducing actual cellular images in their original form.

Thus, representative images of normal cells are shown in FIG. 6, while representative images of carcinoma cells are shown in FIG. 7. In each Figure, each horizontal row includes four simultaneously acquired images of a single cell. Images in columns 61*a* and 71*a* correspond to blue laser side scatter images (i.e., dark field images), images in columns 61*b* and 71*b* correspond to green HLA-FITC fluorescence images, images in columns 61*c* and 71*c* correspond to bright field images, and images in columns 61*d* and 71*d* correspond to red nuclear fluorescence. As described above, the preferred imaging system is capable of simultaneously collecting six different types of images of a single cell (a dark field image, a bright field image, and four fluorescence images); in FIGS. 6 and 7, two of the fluorescence channels have not been utilized. Once again, it should be recognized that FIGS. 6 and 7 have been modified to facilitate their reproduction. As full-color images, the backgrounds of FIGS. 6 and 7 are black, images in columns 61*a* and 71*a* are blue, images in columns 61*b* and 71*b* are green, images in columns 61*c* and 71*c* are grayscale images on a gray background, and images in columns 61*d* and 71*d* are red.

When visually comparing full-color images of FIGS. 6 and 7, it is immediately apparent that images of normal mammary epithelial cells in column 61*c* (the green fluorescence channel) of FIG. 6 are vivid, while images of carcinoma cells in column 71c (the green fluorescence channel) of FIG. 7 can hardly be distinguished. It is also apparent that while none of the dark field images (columns 61a and 71a) are particularly intense, the dark field images (column 61a) of normal mammary epithelial cells in FIG. 6 are significantly more intense than are the dark field images (column 71a) of carcinoma cells in FIG. 7. Yet another qualitative observation that can be readily made is that the average intensity of the red fluorescence images (column 71d) of carcinoma cells in FIG. 7 is substantially greater than the average intensity of the red fluorescence images (column 61d) in FIG. 6.

Initial qualitative observations provided a starting point for the identification of quantitative features that distinguished the two populations. Normal cells were noted to have higher scatter intensity and heterogeneity, generally were larger, and had lower nuclear intensity. The subsequent analysis sought to quantitate these differences, as well as to discover additional parameters that might have discrimination capability. A screen capture of the corresponding IDEAS™ analysis is shown in FIG. 8A.

Figure 8B:
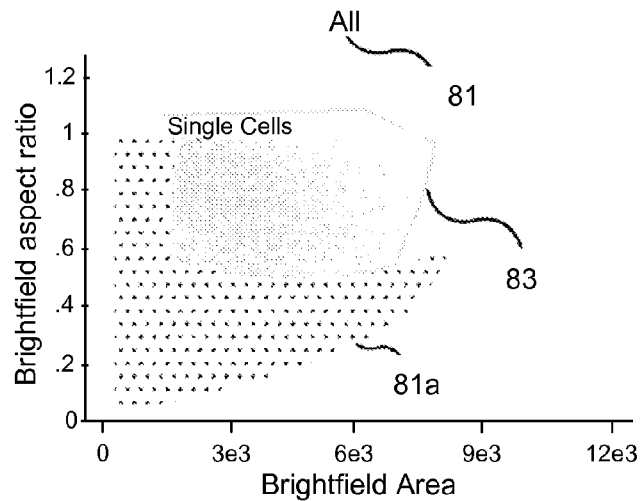
Figure 8C:
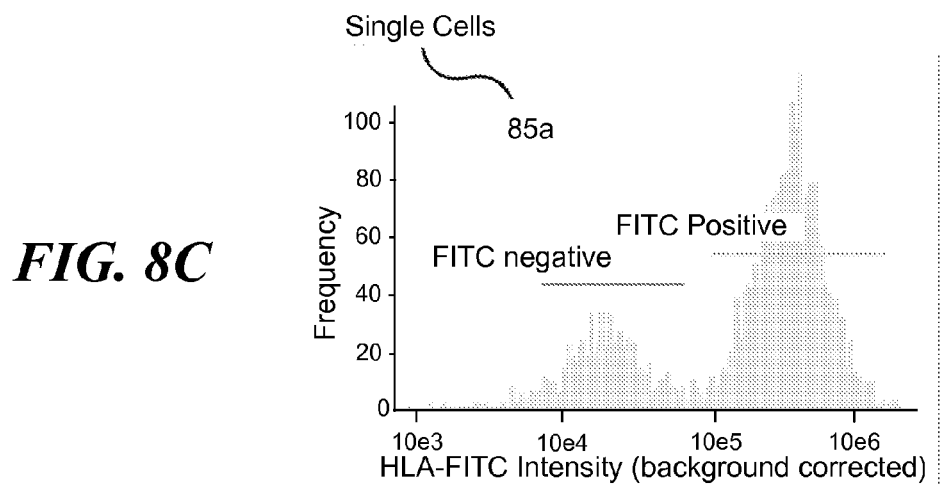
Figure 8D:
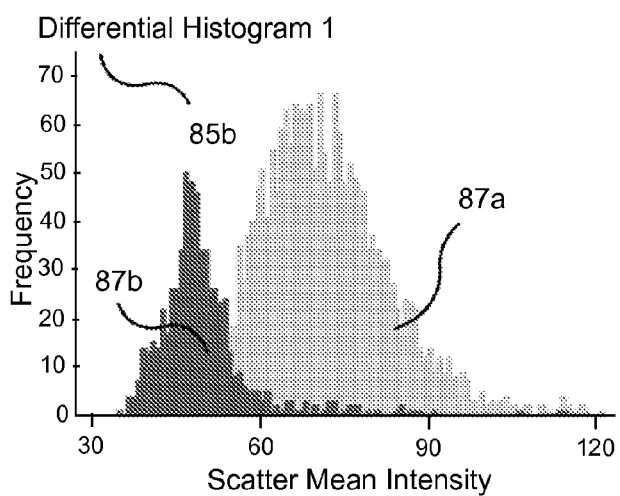
Figure 8E:
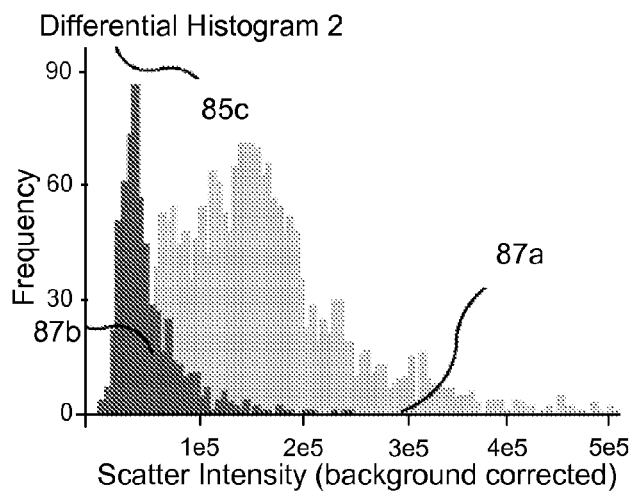
Figure 8F:
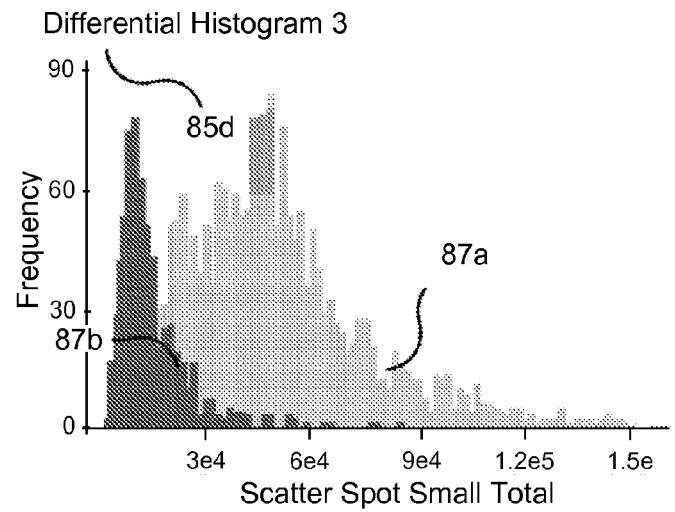

The analysis shown in FIG. 8A proceeded from a dot plot 81 (FIG. 8B) in the upper left of the Figure. Single cells were first identified, based on dot plot 81, which was defined as bright field area versus aspect ratio. A gate (not separately shown) was drawn around the population containing putative single cells based on the criteria of the area being sufficiently large to exclude debris, and the aspect ratio being greater than −0.5, which eliminates doublets and clusters of cells. The veracity of the gating was tested by examining random cells both within and outside of the gate using the click-on-a-dot visualization functionality.

Next, the normal mammary cells were distinguished from the mammary carcinoma cells using the anti-HLA-FITC marker that was applied only to the normal cells. A solid yellow histogram 85a (FIG. 8C) of FITC intensity was generated and is shown to the right of dot plot 81. A gate 83 was then drawn around the FITC positive (normal mammary epithelial cells) and FITC negative (mammary epithelial carcinoma cells), resulting in a subpopulation of 2031 normal cells, and a subpopulation of 611 carcinoma cells. These subpopulations were then used to identify features that quantitatively discriminated between normal and cancerous cells, based on differential histograms. It should be recognized that FIG. 8A has been modified to facilitate its reproduction. As a full-color image, the background of each frame including a cell is black, and the background for each dot plot and histogram is black, to facilitate visualization of the cells and data. This modification resulted in the even distribution of dots 81a, even though such an even distribution was not present in the full color image.

The remaining ten histograms (i.e., histograms 85b-85k; FIGS. 8D-M) in FIG. 8A are differential histograms of the normal cells 87a (shown as green in a full-color image) and carcinoma cells 87b (shown as red in a full-color image), with each histogram representing a different quantitative feature. The ten discriminating features fell into five distinct classes: scatter intensity, scatter texture, morphology, nuclear intensity, and nuclear texture. Differential histograms 85b (FIG. 8D), 85c (FIG. 8E), and 85d (FIG. 8F) demonstrate the difference between the two populations using three different, but correlated, scatter intensity features: "scatter mean intensity" (total intensity divided by cell area), "scatter intensity" (total intensity minus background), and "scatter spot small total" (total intensity of local maxima). Although all three scatter intensity features provided good discrimination, "scatter mean intensity" (histogram 85b) was the most selective.

Figure 8G:
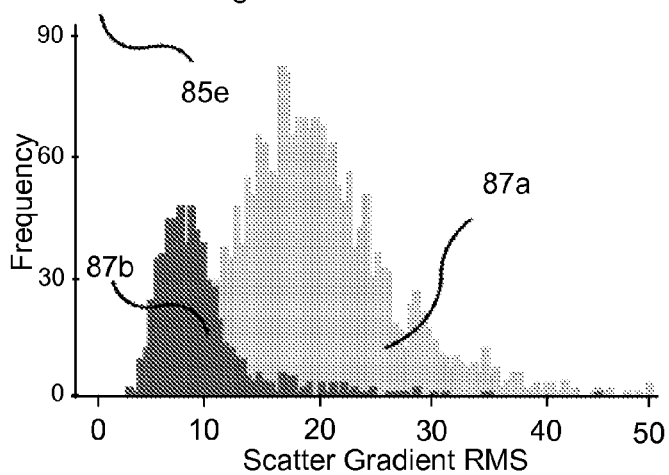
Figure 8H:
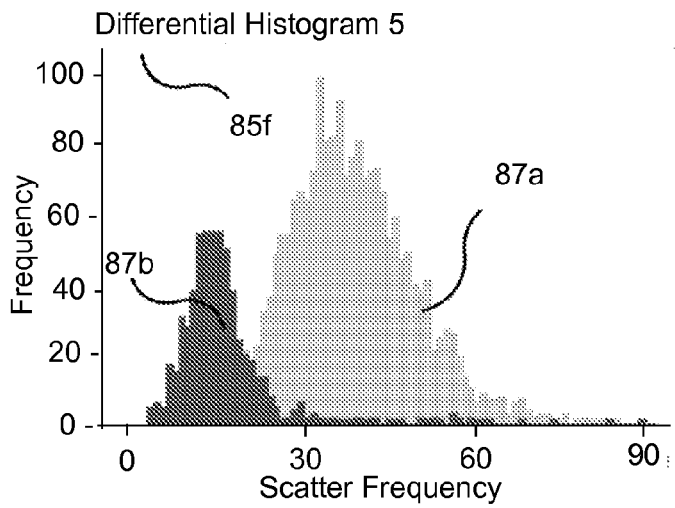

Differential histograms 85e (FIG. 8G) and 85f (FIG. 8H) quantitated scatter texture using either an intensity profile gradient metric ("scatter gradient RMS"; histogram 85e; FIG. 8G) or the variance of pixel intensities ("scatter frequency"; histogram 85f; FIG. 8H), which proved more selective.

Figure 8I:
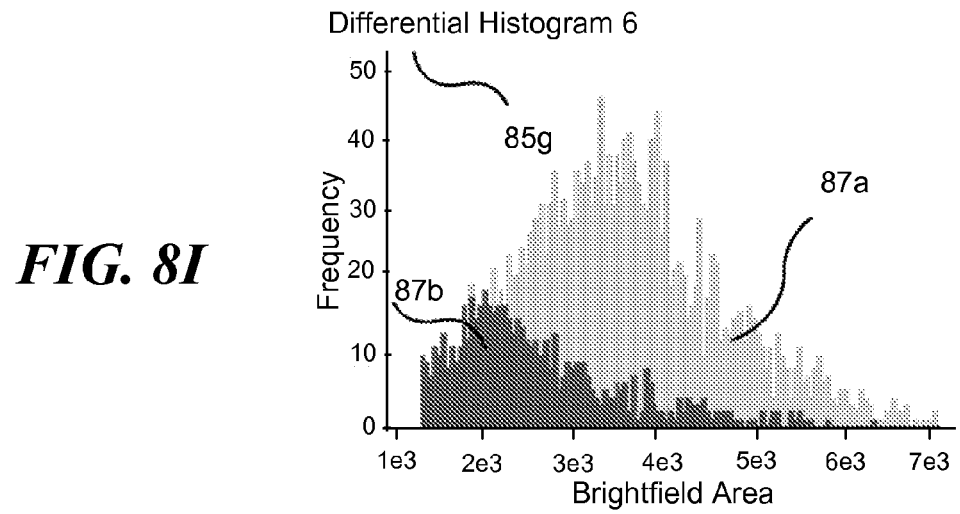
Figure 8J:
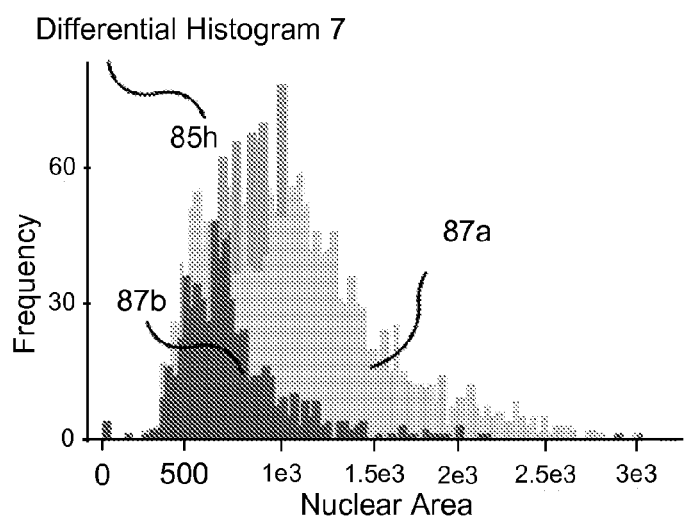
Figure 8K:
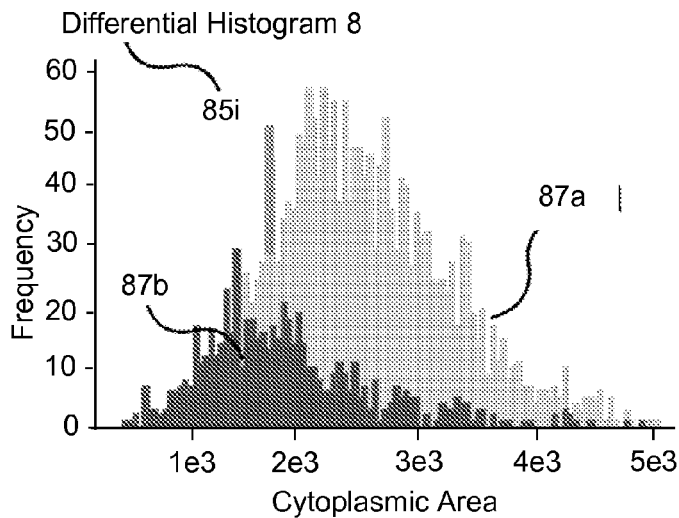
Figure 8L:
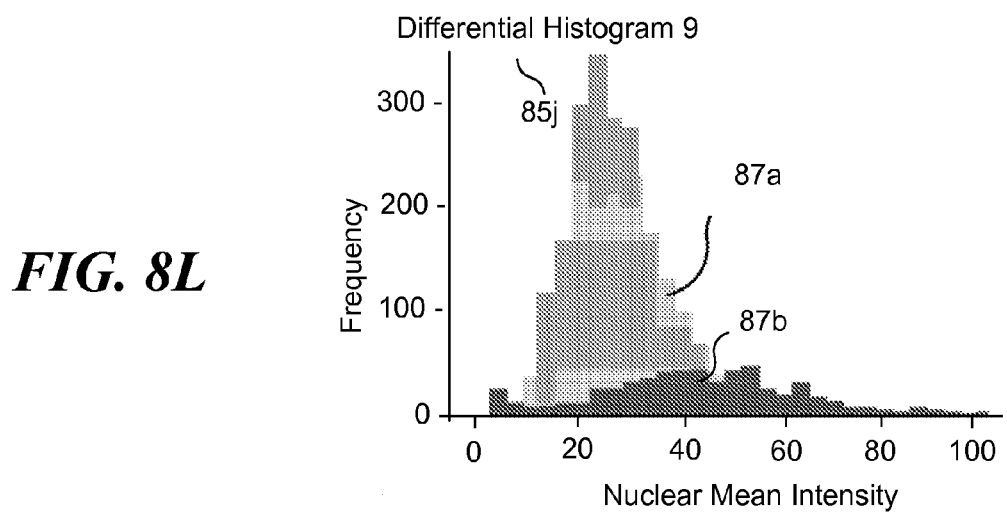

Differential histograms 85g (FIG. 8I), 85h (FIG. 8J) and 85i (FIG. 8K) plotted the cellular area (bright field area, histogram 85g; FIG. 8I), nuclear area (from the DNA fluorescence imagery, histogram 85h; FIG. 8J), and cytoplasmic area (cellular/nuclear area, histogram 85i; FIG. 8K). The carcinoma cell lines were generally smaller in bright field area, confirming the qualitative observations from cell imagery. While the nuclear area of the carcinoma cell lines was proportionately smaller than that of the normal cells (e.g. the Nuclear/Cellular area ratio was not discriminatory), the cytoplasmic area was significantly lower in the carcinoma cells.

Figure 8M:
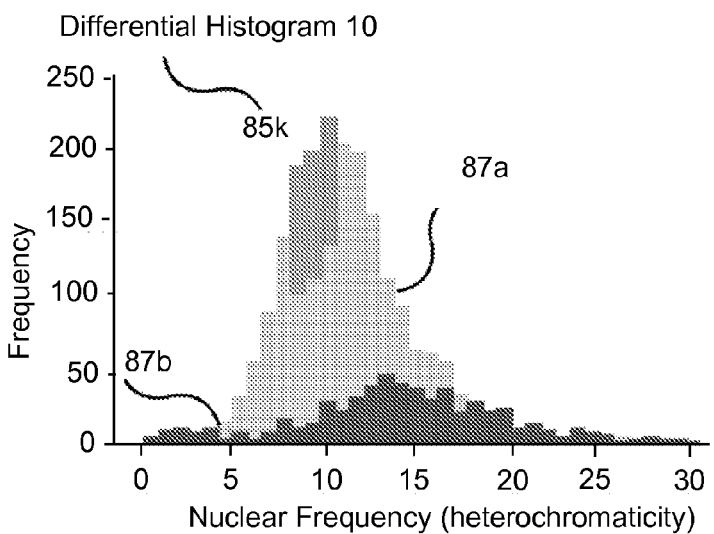

Finally, differential histograms 85j (FIG. 8L) and 85k (FIG. 8M) plotted the nuclear mean intensity (histogram 85j/ FIG. 8L) and nuclear frequency (heterochromaticity, histogram 85k; FIG. 8M), respectively. As in the case of scatter, both of these features provided some discriminatory power.

The multispectral/multimodal imagery collected by the ImageStream™ instrument and analyzed using the IDEAS™ software package in this engineered experiment revealed a number of significant differences in dark field scatter, morphology, and nuclear staining between normal epithelial and epithelial carcinoma cells. While it is well-recognized that cells adapted to tissue culture have undergone a selection process that may have altered their cellular characteristics, these data demonstrate that it is feasible to build an automated classifier that uses the morphometric and photometric features identified and described above to separate normal from transformed epithelial cells, and possibly other cell types.

A further experimental investigation analyzed image data collected from a mixture of normal peripheral blood cells and mammary carcinoma cells. As shown in FIG. 5 (discussed above), cell classification of human peripheral blood can be achieved using a flow imaging system configured to simultaneously obtain a plurality of images of each cell, and using an automatic image analysis program (with the ImageStream™ instrument representing an exemplary imaging system, and the IDEAS™ software package representing an exemplary image analysis program). Using CD45 expression combined with an analysis of dark field light scatter properties, cells can be separated into five distinct populations based on the image data collected by the flow imaging system: lymphocytes, monocytes, neutrophils, eosinophils and basophils. This separation of human peripheral blood into distinct subpopulations is shown in greater detail in FIG. 9, which includes exemplary relative abundance data for the different subpopulations. The veracity of the classifications was determined by using population-specific monoclonal antibody markers and backgating marker-positive cells on the scatter vs. CD45 plot, as well as morphological analysis of the associated imagery. The x-axis of the graph in FIG. 9 corresponds to anti-CD45-FITC Intensity, while the y-axis corresponds to dark field scatter intensity.

In order to determine whether the techniques disclosed herein (utilizing the flow imaging instrument system described above, which is exemplified by the ImageStream™ instrument, and imaging analysis software, which is exemplified by the IDEAS™ software package) could discriminate epithelial carcinoma cells from normal PBMC, an artificial mixture of tumor cells and normal PBMC was produced as described above. The cell mixture was labeled with an anti-CD45-FITC mAb and a fluorescent DNA binding dye in order to differentiate PBMC subpopulations, generally as described above. A comparison of the scatter vs. CD45 bivariate plots for normal peripheral blood mononuclear cells and the PBMC sample spiked with the carcinoma cells is shown in FIGS. 10A and 10B. FIG. 10A graphically illustrates a distribution of normal peripheral blood mononuclear cells (PBMC) based on image data collected from a population of cells that does not include mammary carcinoma cells. FIG. 10B graphically illustrates a distribution of normal PBMC and mammary carcinoma cells based on image data collected from a population of cells that includes both cell types, illustrating how the distribution of the mammary carcinoma cells is distinguishable from the distribution of the normal PBMC. In this analysis, carcinoma cells 101a fall well outside of a normally defined PBMC population 101b, as confirmed by visual inspection of the outlier population.

As shown in FIGS. 11A and 11B, carcinoma cells 111a can also be discriminated from normal PBMC 111b using some of the morphometric and photometric features identified in FIGS. 8A-8M (e.g., nuclear area, cytoplasmic area, scatter intensity, and scatter frequency). FIG. 1A graphically illustrates a distribution of normal PBMC and mammary carcinoma cells based on measured cytoplasmic area derived from image data collected from a population of cells that includes both cell types, illustrating how the distribution of cytoplasmic area of mammary carcinoma cells is distinguishable from the distribution of cytoplasmic area of the normal PBMC. FIG. 11B graphically illustrates a distribution of normal PBMC and mammary carcinoma cells based on measured scatter frequency derived from image data collected from a population of cells that includes both cell types, illustrating how the distribution of the scatter frequency of the mammary carcinoma cells is distinguishable from the distribution of the scatter frequency of the normal PBMC. Although these features were initially identified for the purpose of discriminating between normal mammary and mammary carcinoma cells, they provide a high level of discrimination between mammary epithelial carcinoma cells and PBMC. Significantly, normal epithelial cells would be even more clearly differentiated from PBMC and distinct from the epithelial carcinoma cells using these parameters.

It should be recognized that FIGS. 10A, 10B, 11A, and 11B have been modified to facilitate their reproduction. As a full-color images, the background of each frame including a dot plot is black, to facilitate visualization of the cells and/or data, and dots representing PBMC and carcinoma cells are different colors.

The results noted above were verified by visual inspection of the segregated images (i.e., the images separated into subpopulations corresponding to carcinoma cells and healthy cells using one or more of the above-identified photometric and/or morphometric parameters). Image gallery data were produced from the spiked PBMC data described above. FIG. 12 includes representative images from the carcinoma cell population, obtained using an overlay composite of bright field and DRAQ5 DNA fluorescence (red, with the image processing being performed by the image analysis software). FIG. 13 includes images of the five peripheral blood mononuclear cell populations defined using dark field scatter, CD45 (green), and DRAQ5 (red) for nuclear morphology. Note that the two Figures are at different size scales. It should be recognized that FIG. 12 has been modified to facilitate its reproduction. As a full-color image, the background of FIG. 12 is black, the background of each frame including a cell is brown/gray, and the nucleus of each cell is red. FIG. 13 has been similarly modified to facilitate its reproduction. As a full-color image, the background of FIG. 13 is black, the periphery of each cell is green, and the nucleus of each cell is red.

Significantly, the above studies demonstrate the feasibility of optically discriminating a subpopulation of normal epithelial cells from a subpopulation of transformed cells by analyzing multi-spectral/multimodal image data from a mixed population of such cells, where the image data are simultaneously collected. The above studies also demonstrate the feasibility of detecting epithelial carcinoma cells in blood by analyzing multi-spectral/multimodal image data from a mixed population of such cells, where the image data are simultaneously collected.

Exemplary Computing Environment

As noted above, an aspect of the present invention involves image analysis of a plurality of images simultaneously collected from members of the population of cells. Reference has been made to an exemplary image analysis software package. FIG. 14 and the following related discussion are intended to provide a brief, general description of a suitable computing environment for practicing the present invention, where the image processing required is implemented using a computing device generally like that shown in FIG. 14. Those skilled in the art will appreciate that the required image processing may be implemented by many different types of computing devices, including a laptop and other types of portable computers, multiprocessor systems, networked computers, mainframe computers, hand-held computers, personal data assistants (PDAs), and on other types of computing devices that include a processor and a memory for storing machine instructions, which when implemented by the processor, result in the execution of a plurality of functions.

An exemplary computing system 150 suitable for implementing the image processing required in the present invention includes a processing unit 154 that is functionally coupled to an input device 152, and an output device 162, e.g., a display. Processing unit 154 include a central processing unit (CPU 158) that executes machine instructions comprising an image processing/image analysis program for implementing the functions of the present invention (analyzing a plurality of images simultaneously collected for members of a population of objects to enable at least one characteristic exhibited by members of the population to be measured). In at least one embodiment, the machine instructions implement functions generally consistent with those described above, with reference to the flowchart of FIG. 3, as well as the exemplary screenshots. Those of ordinary skill in the art will recognize that processors or central processing units (CPUs) suitable for this purpose are available from Intel Corporation, AMD Corporation, Motorola Corporation, and from other sources.

Also included in processing unit 154 are a random access memory 156 (RAM) and non-volatile memory 160, which typically includes read only memory (ROM) and some form of memory storage, such as a hard drive, optical drive, etc. These memory devices are bi-directionally coupled to CPU 158. Such storage devices are well known in the art. Machine instructions and data are temporarily loaded into RAM 156 from non-volatile memory 160. Also stored in memory are the operating system software and ancillary software. While not separately shown, it should be understood that a power supply is required to provide the electrical power needed to energize computing system 150.

Input device 152 can be any device or mechanism that facilitates input into the operating environment, including, but not limited to, a mouse, a keyboard, a microphone, a modem, a pointing device, or other input devices. While not specifically shown in FIG. 14, it should be understood that computing system 150 is logically coupled to an imaging system such as that schematically illustrated in FIG. 1A, so that the image data collected are available to computing system 150 to achieve the desired image processing. Of course, rather than logically coupling the computing system directly to the imaging system, data collected by the imaging system can simply be transferred to the computing system by means of many different data transfer devices, such as portable memory media, or via a network (wired or wireless). Output device 162 will most typically comprise a monitor or computer display designed for human visual perception of an output image.

High-Throughput, EDF Imaging of Cells Subjected to In Situ Hybridization

Imaging flow cytometry is compatible with the broad range of cell-staining protocols developed for conventional flow cytometry and those developed for imaging cells on slides, although with protocol modifications to the suspension format. Fluorescence in situ hybridization (FISH) is recognized as a slide-based imaging application that could benefit greatly from the greater throughput and quantitative identification of flow cytometry; several groups have adapted hybridization techniques to cells in suspension. The lack of spatial resolution in standard flow cytometry, however, requires the substitution of total probe intensity for spot counting as a means of assessing results, thereby preventing the use of flow cytometry for the analysis of translocations, inversions, or other rearrangements. Although there are certain specific FISH applications that have strong and consistent signals, such as telomeric length analysis or the detection of the presence or absence of a Y chromosome, FISH probe intensity variation can be high and signal intensities often approach the detection limits of standard flow cytometry, reducing the reliability of aneuploidy assessment.

Imaging flow cytometry is potentially well suited to FISH analysis because the detection limit of imaging flow cytometry improves as the size of the fluorescent signal source decreases. Further, the quantitative capabilities of FISH-probed cells for applications such as aneuploidy analysis, is accomplished by spot counting rather than by relying exclusively on total intensity analysis, making it tolerant of wide variations in probe intensity and more consistent with the standard of practice in clinical FISH assessment.

To investigate the usefulness of imaging flow cytometry for clinical FISH analysis, human peripheral blood mononuclear cells (PBMC) were obtained (AllCells, Emeryville, Calif.) and probed using a FISH in suspension (FISHIS) protocol developed at Amnis Corporation. The cells were fixed and permeabilized with successive incubations in 30% Carnoy's solution in PBS (30 minutes at 4° C.), then 70% Carnoy's solution in PBS (10 minutes at 4° C.). After centrifugation, the cells were washed once in 2× saline sodium citrate (SSC), then resuspended in hybridization buffer containing the SpectrumGreen-labeled chromosome 12 enumeration probe according to the manufacturer's directions (Vysis, Des Plaines, Ill.). To hybridize the probe, cells in polymerase chain reaction tubes were exposed to 80° C. for 5 minutes and 42° C. for 2 hours in a DNA thermocycler. One hundred micro-liters of 2×SSC was added to the tubes and the cells pelleted by centrifugation. Cells were resuspended in 0.4× SSC containing 0.3% NP40 and exposed to 72° C. for 2 minutes. The cells were centrifuged and the pellets then resuspended in 50 micro-liters of 1% paraformaldehyde (in PBS). The sample was then loaded into the ImageStream™ system, and a file of 3500 cells was collected.

FIG. 15 is a gallery of 15 individual cells from the PBMC data file, numbered by the order in which they flowed through the instrument. Each cell is represented by a row of images (left to right): dark field, chromosome 12 fluorescence, bright field, and an overlay of the fluorescence and bright-field images. Doublets and larger clusters were eliminated from the analysis by plotting the area versus the aspect ratio of each cell's bright field image on a dot plot and gating on single cells, which represented approximately 60% of the data and were differentiated clearly as a population having an aspect (length-to-width) ratio close to one and lower area than doublets and clusters. No other pre-selection was performed, so the gallery represents an unbiased sampling of FISH data in PBMC populations. Most cells had two well-resolved FISH spots, corresponding to the two copies of chromosome 12. A fraction of the cells, however, had one or both FISH spots out of focus to some degree or only one apparent spot corresponding to a cell orientation that superimposed the FISH spots from the perspective of the imaging system. Defocus is a problem that increases with cell size, whereas the frequency of FISH spot superposition tends to decrease as cell size increases. The cells in the PBMC data file were found to have a mean diameter of 6.4±0.7 micrometers, which is small compared with the nuclear size of many epithelial cell types.

It should be recognized that FIG. 15 has been modified to facilitate its reproduction. As a full-color image, the background of FIG. 15 is black, the background of each frame including a cell is brown/gray, the cellular images in the dark field column are blue, and the FISH spots in the second and fourth columns are green (not purple).

To address the constraint that limited depth of field places on FISH analysis in larger cells assessed by imaging flow cytometry, a prototype ImageStream™ system having extended depth-of-field (EDF) image collection capabilities was developed. The EDF version of the ImageStream™ system incorporates a specialized optical element in the standard optical system that causes light from widely different focal positions in the object to be imaged on the detector plane simultaneously in a process referred to as Wavefront Coding™ by its developer (CDM Optics, Boulder, Colo.). The modified imagery is post processed to recover image sharpness while preserving the increased depth of focus that comes from the modification of the wavefront during data acquisition. Images acquired using the EDF version of the system have an effective depth of field of approximately 15 micrometers, resulting in a high-resolution image of the cell with all features simultaneously in focus. Unlike confocal image stacking techniques, the Wavefront Coding™ methodology enables image acquisition at rates of hundreds of cells per second.

To compare FISH imagery in the standard and EDF Image Stream™ configurations, Jurkat human lymphoma cells (ATCC) were grown in suspension culture, hybridized to a chromosome 8 probe (Vysis) using the FISHIS protocol (described previously), and imaged using the EDF and standard ImageStream™ configurations. FIGS. 16 and 17 illustrate galleries of standard and EDF images, respectively, of hybridized Jurkat cells classified as disomic for chromosome 8. In both galleries, each cell is represented by an overlay of its FISH spot fluorescence image (green) on its reduced-contrast bright field image acquired at the same time. Because Jurkats are known to exhibit cytogenetic instability, only single cells were included in each gallery based on their automated classification as having two chromosome 8 FISH spots, but no subjective selection criteria were used in selecting the 25 images shown in each Figure. The degree of FISH spot focus enhancement with EDF imaging is qualitatively evident and improves the fidelity of automated spot analysis features (peak intensity, spot size, mean separation distance, and so forth) by as much as tenfold.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for detecting cancer or a precancerous condition from images collected from a population of cells present in a bodily fluid, comprising the steps of:
   (a) providing a first population of abnormal cells and a second population of normal cells, the abnormal cells comprising at least one type of cells selected from the group consisting of cancer cells and cancer precursor cells;
   (b) imaging the first population of cells in flow to collect first image data, and imaging the second population of cells in flow to collect second image data, such that the first and second image data for each cell in the respective populations of cells includes a plurality of simultaneously collected images, the plurality of simultaneously collected images for each cell comprising at least one of the following two types of images:
      (i) multispectral images; and
      (ii) multimodal images;
   (c) analyzing the first and second image data to identify at least one cell characteristic that can be measured using the first and second image data and that enables the abnormal cells to be distinguished from the normal cells;
   (d) collecting a bodily fluid comprising a third population of cells;
   (e) imaging the third population of cells in flow to collect third image data, such that the third image data for each cell includes a plurality of simultaneously collected images, the plurality of simultaneously collected images comprising at least one of the following two types of images:
      (i) multispectral images; and
      (ii) multimodal images; and
   (f) analyzing the third image data to determine if any abnormal cells are present in the third population, by determining if the at least one cell characteristic that enables the abnormal cells to be distinguished from the normal cells is present in the third image data, the presence of abnormal cells indicating the presence of cancer or a precancerous condition.

2. The method of claim 1, further comprising the step of staining at least one of the first population and the second population, to facilitate distinguishing the first image data from the second image data, even when the first population and the second population are combined before imaging.

3. The method of claim 1, wherein the step of identifying the at least one cell characteristic comprises the step of identifying a photometric parameter.

4. The method of claim 1, wherein the step of identifying the at least one cell characteristic comprises the step of identifying a morphometric parameter.

5. The method of claim 4, wherein the step of identifying the morphometric parameter comprises the step of identifying a cytoplasmic area.

6. The method of claim 5, wherein the step of identifying the cytoplasmic area comprises the steps of:
   (a) using a bright field image to determine a cellular area;
   (b) using a fluorescent image to determine a nuclear area; and
   (c) defining the cytoplasmic area as a difference between the cellular area and the nuclear area.

7. The method of claim 1, wherein the step of identifying the at least one cell characteristic comprises the step of identifying at least one of the following characteristics:
   (a) a scatter intensity;
   (b) a scatter texture;
   (c) a nuclear intensity; and
   (d) a nuclear texture.

8. The method of claim 1, wherein the step of identifying the at least one cell characteristic comprises the step of identifying a mean scatter intensity, the mean scatter intensity being calculated using a total intensity divided by a cellular area.

9. The method of claim 1, wherein the step of identifying the at least one cell characteristic comprises the step of calculating a scatter intensity by removing a background intensity from a total intensity.

10. The method of claim 1, wherein the step of identifying the at least one cell characteristic comprises the step of calculating a scatter intensity by determining a total intensity of local scatter maxima.

11. The method of claim 1, wherein the step of identifying the at least one cell characteristic comprises the step of identifying a scatter texture using at least one technique selected from the group consisting of:
    (a) identifying an intensity profile gradient metric; and
    (b) identifying a variance of pixel intensities.

12. The method of claim 1, wherein the plurality of simultaneously collected images acquired for the first, second, and third populations comprise extended depth of field images.

13. The method of claim 1, wherein the plurality of simultaneously collected images acquired for the first, second, and third populations comprise at least two types of images selected from the group consisting of: a bright field image, a dark field image, and a fluorescent image.

14. An imaging system configured to acquire and analyze image data collected from a population of cells, to enable a cancerous or precancerous condition to be detected, comprising:
    (a) an image acquisition subsystem configured to simultaneously acquire a plurality of images of individual cells from the population of cells, while there is relative movement between the image acquisition subsystem and an individual cell, the plurality of images comprising at least two types of images selected from the group consisting of:
       (i) a bright field image;
       (ii) a dark field image; and
       (iii) a fluorescent image;
    (b) a database including at least one cell characteristic indicative of an abnormal condition, where the abnormal condition comprises at least one condition selected from the group consisting of a cancerous condition, and a precancerous condition, and where the at least one cell characteristic can be measured using the plurality of images acquired by the image acquisition subsystem; and
    (c) a processor configured to analyze the plurality of images of individual cells to determine if the at least one cell characteristic is present in the population of cells.

15. The system of claim 14, wherein the at least one characteristic comprises a photometric parameter.

16. The system of claim 14, wherein the at least one characteristic comprises a morphometric parameter.

17. The system of claim 16, wherein the morphometric parameter comprises cytoplasmic area.

18. The system of claim 15, wherein the at least one characteristic comprises at least one element selected from a group consisting of:
   (a) a scatter intensity;
   (b) a scatter texture;
   (c) a nuclear intensity; and
   (d) a nuclear texture.

19. The system of claim 15, wherein the at least one characteristic comprises at least one element selected from a group consisting of:
   (a) a mean scatter intensity, the mean scatter intensity being calculated using a total intensity divided by a cellular area;
   (b) a scatter intensity calculated by removing a background intensity from a total intensity; and
   (c) a scatter intensity calculated by determining a total intensity of local scatter maxima.

20. An imaging system configured to acquire and analyze image data collected from a population of cells, where the image data include a plurality of images of individual cells that are acquired simultaneously, to enable a cancerous or precancerous condition to be detected, comprising:
   (a) a collection lens disposed so that light traveling from an individual cell passes through the collection lens and travels along a collection path;
   (b) a spectral separation element disposed in the collection path so as to spectrally separate light that has passed through the collection lens, thereby producing spectrally separated light;
   (c) an imaging lens disposed to focus the spectrally separated light, producing focused spectrally separated light;
   (d) a detector disposed to receive the focused spectrally separated light, such that the focused spectrally separated light incident on the detector simultaneously comprises a plurality of images of the individual cell, the plurality of images comprising the image data, the plurality of images being dispersed across the detector such that the plurality of images do not overlap, and the plurality of images being dispersed in a direction orthogonal to a direction of motion of the plurality of images across the detector when there is relative movement between the individual cell and the imaging system; and
   (e) a processor configured to analyze the image data for the plurality of images collected for individual cells in the population of cells, to determine if the image data indicate that any individual cell in the population of cells exhibits the cancerous or precancerous condition.

21. A method for detecting cancer or a precancerous condition from images collected from a population of cells present in a bodily fluid, comprising the steps of:
   (a) providing a first population of abnormal cells and a second population of normal cells, the abnormal cells comprising at least one type of cells selected from the group consisting of cancer cells and cancer precursor cells;
   (b) imaging each cell in the first population of cells while each cell is in flow to collect first image data, and imaging each cell in the second population of cells while each cell is in flow to collect second image data, such that the step of imaging each cell comprises the steps of:
      (i) spectrally dispersing light from the cell into a plurality of light beams having different spectral content; and
      (ii) directing focused light from each of the plurality of light beams having different spectral content onto a different region of a pixilated detector, thereby simultaneously acquiring a plurality of different images of the cell on the pixilated detector, each different image being formed from a different one of the plurality of light beams having different spectral content, the plurality of simultaneously collected images for each cell comprising at least one of the following two types of images:
         (A) multispectral images; and
         (B) multimodal images;
   (c) analyzing the first and second image data to identify at least one cell characteristic that can be measured using the first and second image data and that enables the abnormal cells to be distinguished from the normal cells;
   (d) collecting a bodily fluid comprising a third population of cells;
   (e) imaging the third population of cells in flow to collect third image data, such that the third image data for each cell includes a plurality of simultaneously collected images, the plurality of simultaneously collected images comprising at least one of the following two types of images:
      (i) multispectral images; and
      (ii) multimodal images; and
   (f) analyzing the third image data to determine if any abnormal cells are present in the third population, by determining if the at least one cell characteristic that enables the abnormal cells to be distinguished from the normal cells is present in the third image data, the presence of abnormal cells indicating the presence of cancer or a precancerous condition.

* * * * *